(12) United States Patent
Roberge

(10) Patent No.: US 10,657,220 B2
(45) Date of Patent: May 19, 2020

(54) SYSTEM AND METHODS FOR MEDICAL REPORTING

(71) Applicant: ASCEND HIT LLC, Lisle, IL (US)

(72) Inventor: James Roberge, Highland Park, IL (US)

(73) Assignee: ASCEND HIT LLC, Lisle, IL (US)

(*) Notice: Subject to any disclaimer, the term of this patent is extended or adjusted under 35 U.S.C. 154(b) by 1120 days.

(21) Appl. No.: 14/693,117

(22) Filed: Apr. 22, 2015

(65) Prior Publication Data

US 2016/0314246 A1  Oct. 27, 2016

(51) Int. Cl.
*A61B 17/70* (2006.01)
*A61B 90/00* (2016.01)
(Continued)

(52) U.S. Cl.
CPC ........... *G06F 19/321* (2013.01); *G16H 10/60* (2018.01); *G16H 15/00* (2018.01); *G16H 30/20* (2018.01)

(58) Field of Classification Search
CPC ........... A61N 1/08; G06F 17/30; G06F 19/30; G06F 19/32; G06F 19/321; G06F 19/324; G06F 19/325; G06F 19/326; G06F 19/328; G06F 19/34; G06F 19/3418; G06F 19/3456; G06F 19/3462; G06F 19/3468; G06F 19/3475; G06F 19/3481; G06F 19/36; G06Q 10/10; G06Q 40/08; G06Q 50/22; G06Q 50/24; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 30/20; G16H 30/40; G16H 40/00; G16H 40/20; G16H 40/40; G16H 40/60; G16H 40/63; G16H 40/67; G16H 50/00; G16H 50/20; G16H 50/30; G16H 50/50; G16H 50/70;
(Continued)

(56) References Cited

U.S. PATENT DOCUMENTS

2012/0020536 A1  1/2012  Moehrle
2014/0257854 A1* 9/2014  Becker .................. G06F 19/321
                                                   705/3

* cited by examiner

*Primary Examiner* — Maroun P Kanaan
(74) *Attorney, Agent, or Firm* — Valauskas Corder LLC

(57) ABSTRACT

The present invention relates generally to a system and methods for medical reporting. More specifically, the invention is directed to a system that includes a structured reference frame component through the use of which one or more anatomical features or pathologies that are shown on an actual image taken of a patient can be associated with the data and other information provided in a structured knowledge base. Certain embodiments of the system include a structured reference frame component that can be used for a plurality of medical images taken of a patient, the plurality of images being ones taken, for example, of different views or projections or at different times to provide what is termed for purposes of this application a structured image set. Advantageously, such a structured image set places the subject anatomical feature or pathology in a greater spatial and/or temporal context. Additionally, embodiments of the invention allow users through the use of structured image set to annotate, augment, and overall interact with the clinically more accurate and detailed medical image, not the conventional anatomical cartoons.

20 Claims, 28 Drawing Sheets

(51) Int. Cl.
  *G06T 7/168* (2017.01)
  *G06F 19/00* (2018.01)
  *G16H 10/60* (2018.01)
  *G16H 15/00* (2018.01)
  *G16H 30/20* (2018.01)

(58) Field of Classification Search
  CPC ........ G16H 50/80; G16H 70/00; G16H 70/20; G16H 70/14; G16H 70/60; G16H 80/00; G06T 7/0012; G06T 7/11; G06T 2207/30004; G06T 2210/41; G06T 7/12
  See application file for complete search history.

↳ 2380A

↳ 2380B

2480A

2480B

US 10,657,220 B2

SYSTEM AND METHODS FOR MEDICAL REPORTING

FIELD OF THE INVENTION

The present invention relates generally to a system and methods for medical reporting. More specifically, the invention is directed to a system that includes a structured reference frame component through the use of which one or more anatomical features or pathologies that are shown on an actual image taken of a patient can be associated with the data and other information provided in a structured knowledge base. Certain embodiments of the system include a structured reference frame component that can be used for a plurality of medical images taken of a patient, the plurality of images being ones taken, for example, of different views or projections or at different times to provide what is termed for purposes of this application a structured image set. Advantageously, such a structured image set places the subject anatomical feature or pathology in a greater spatial and/or temporal context. Additionally, embodiments of the invention allow users through the use of structured image set to annotate, augment, and overall interact with clinically more accurate and detailed medical images, not the conventional anatomical cartoons.

BACKGROUND

The diagnosis of a patient's condition often relies on the use of medical images. Medical images (e.g., X-ray, CT, MRI, and ultrasound images) are intended to provide a detailed view of a patient's anatomy. Once captured, a trained health care worker—such as a trained cardiologist or radiologist—reviews the one or more medical images taken of a patient and prepares a report of what the images appear to show in order to diagnose possible pathologies, determine possible approaches to treatment, and guide and evaluate the results of treatment.

There are a variety of known approaches by which reports based on the review of medical images can be created. One conventional approach—that may use dictation and voice recognition—can produce free-text narrative reports with little or no coded data. Another conventional approach—in which a physician records coded data elements and from which the reporting system generates report narrative—is termed structured reporting.

Many of the known clinical reporting systems permit a drawing to be prepared and included as part of the report. In certain known clinical reporting systems, the drawing can be very basic and can consist of a simple line drawing depicting anatomical features that may be commonly found in a hypothetical model patient. A health care worker uses the simple anatomical cartoon typically to record the worker's observations, thoughts, and conclusions while reviewing the separate medical images taken of a patient's actual anatomy. Onto the simple drawing, the worker can apply text annotations to explain what is seen in the separate medical patient images. Some known reporting systems allow a worker to make free-form modifications via basic drawing operations (e.g., draw line, fill region, erase line/region onto a simple lined drawing).

The disadvantage of such reporting systems is that the worker must work back and forth with at least two images—the medical image or images taken of the patient and the simple drawing—in order to produce the annotated/modified simple drawing. This process is inherently inefficient and can create errors. Another disadvantage is that, while the resulting annotated/modified drawing does provide information to the human reader, the information cannot be further processed or analyzed by computerized systems.

Additional known reporting systems permit recorded coded data to be associated with anatomical features depicted on a simple drawing. FIG. 1 through FIG. 4 illustrate versions of a simple drawing and FIG. 5 illustrates an image of the coronary arteries from a known clinical reporting system.

FIG. 1 illustrates a simple drawing of the coronary arteries 10. FIG. 2 illustrates a modified coronary arteries drawing 20, the modifications being based on the recorded coded data 21, Specifically, the modified coronary arteries drawing 20 illustrates the position of a stenotic lesion in the right coronary artery (RCA) symbolized through the insertion of matching thickened lines in the drawing 23 and variations in the branching pattern of the coronary vessels 22. The arrowheads of the lines extending from the number "22" in FIG. 2 show the variations—that is, the portions of the coronary vessels illustrated in the FIG. 1 model drawing 10 that were not found in the patient whose examination was the subject of the recorded coded data 21. FIG. 2 also includes a text label 24 that provides certain of the information from the recorded data 21 regarding that which is shown in the simplified drawing (that is, the amount of stenosis caused by the stenotic lesions in the RCA).

FIG. 3 illustrates a coronary artery drawing 30 producible by a known reporting system that allows a user (e.g., a health care worker) to select a component shown in the drawing—in this example, the Left Anterior Descending Artery, or "LAD", the selection illustrated in FIG. 3 by the large arrowhead and the partial asterisk shape—, and enter certain data regarding it in a data form 32.

FIG. 4 illustrates another modified coronary arteries drawing 40 producible by a known reporting system that shows extensive modification by a user (such as a health care worker) of the original simple line drawing 10 shown in FIG. 1 in an attempt to more accurately represent the patient's condition. Specifically, modified drawing 40 includes "L"s and thickened dark lines 41 to show coronary lesions, thin vessels marked with "CS" 42 to show collateral circulation, and vessels marked with large "X"s 43 to show that the patient's heart does not have these vessels.

It is clear that, while reporting systems that utilize simple drawings have been widely used, many disadvantages are associated with them. Many such disadvantages, discussed in part above, are produced because the starting point for these systems is a simplified drawing of an anatomy of interest. The health care worker must modify this simplified drawing in an attempt to show what is actually occurring in a patient. The modification process is time consuming and an overall inefficient use of resources and one in which errors in the depictions may arise. The cartoon-like drawings do not present the breadth nor the depth of detail conveyed in the patient's actual medical images nor the physiological/pathological status gathered from such images. The lack of detail may present a challenge to the referring physician to accurately diagnose and treat a patient. While the known illustrated anatomical cartoons may express patient-specific anatomical and pathological variations encountered in medical practice, the result is a very complicated diagram that is very difficult to interpret clinically.

Another known approach illustrated in FIG. 5 permits a user to select a location—or "Region of Interest" 51—on a patient's medical image 50 and enter, for example, a measurement 52 or free text annotation 53. In some known reporting systems, the recorded measurement or free-text annotation may be stored with the medical image. However, these additional components typically remain isolated pieces of information about a particular pixel region on the image. The reporting system does not link the recorded information 52, 53 to the anatomical features and pathologies shown in the image or to the data descriptors associated with these anatomical features and pathologies. Without such linkages, the reporting system is incapable of automatically retrieving or recording clinical data related to the specific anatomical features or pathologies shown in a set of medical images and is incapable of automatically displaying such data at the appropriate locations on the appropriate images for review by a physician—including displaying iconography, drawings, callouts, or notifications derived from such data.

Clearly there is a need for a system and methods by which accurate information regarding the condition of a patient can be recorded and a meaningful report of such condition produced efficiently and with reduced likelihood of errors. The present invention satisfies these demands.

SUMMARY OF THE INVENTION

The present invention relates generally to a system and methods that includes a structured reference frame component through the use of which one or more anatomical features or pathologies that are shown on one or more actual images taken of a patient (for example, a X-ray, CT, MRI, ultrasound, or other image) can be associated with the data and other information about the patient that may be provided in a structured knowledge base. Advantageously, certain embodiments of the present invention can be used to produce a structured reference frame that transforms a patient image from a collection of pixels into a structured image that can interoperate with structured data about a patient.

In the certain embodiments of the system, the structured reference frame component may be used with a plurality of medical images taken, for example, of different views or projections or at different times of a patient—termed a "structured image set" for purposes of this application. Advantageously, a structured image set may place the subject anatomical feature or pathology in a greater spatial and/or temporal, or "spatiotemporal" context (for example, before and after medical treatment). Embodiments of the structured reference frame may specify both the images that comprise the structured image set that are associated with a given anatomical feature or pathology and the spatial characteristics (e.g., position, length, contour, area, shape, volume) of the feature or pathology in each associated image.

Embodiments of the present invention may include a structured data schema—or structured knowledge base—that may be associated with the structured image set through the structured reference frame. The structured knowledge base may provide, for example, generalized information related to the medical condition that is shown in the image set taken of the patient or specific information—such as information and data regarding the patient's medical history and a list of potential treatments—or a combination of these different sets of information.

To allow information to be quickly and easily accessed while viewing one or more of the images in a structured image set, certain embodiments of the invention allow a user to access and enter information in a data entry form that can be linked to a particular location or feature shown in the image. Upon entering a selection of a particular location or feature on the one or more images—such as through a mouse click or keyboard press or "rolling over" the location or feature—the information entered into the data entry form regarding that location or feature can be seen by the user. The data entry form may include any of a variety of data entry controls such as pick lists, checkboxes, numeric boxes, text boxes, and buttons, as well as mechanisms for displaying subordinate or lateral data entry forms such as pop-ups, pop-overs, splits/merges, and dissolves/replaces. The information recorded through the data entry form—termed "structured data" for purposes of this application—may allow a narrative of the recorded data to be prepared such as for a report. Certain embodiments of the present invention may automatically produce the narrative from the information entered into the data entry form. Certain embodiments of the present invention may automatically revise the narrative and the resultant report as the information that is recorded in the data entry form is revised.

Certain embodiments of the present invention may permit information to be entered by voice into the structured knowledge base for a particular location or feature shown in the one or more images. To facilitate such entry of information via voice, the structured reference frame component may include textual identifiers for the anatomical features and pathologies associated with an image in addition to the spatiotemporal characteristics.

In certain embodiments, the structured image set's reference frame can be applied at different levels of spatiotemporal resolution, resulting in different levels of functionality. The more fine-grained the spatial resolution, the more expressive the reference frame may become. This will allow for more specific anatomical features or pathologies to be viewed as well as allow for more detailed callout boxes describing the anatomy and/or functionality or data entry forms for recording or modifying data related to said descriptions.

In certain embodiments, one or more structured image sets may be displayed on a screen, included in a clinical report, or added to a file of the original image set for later review and use. The one or more structured image sets may be additionally be sent to other practitioners or to the patient, depending on the needs of these additional users.

In certain embodiments, a structured image set's reference frame may incorporate complex descriptive iconography, drawings, callouts, and captions, the position and nature of which may be derived from the structured data set. Certain embodiments of the present invention permit a user to select and position the descriptive material for a structured data set on the associated structured reference frames as desired by the user to provide as much medical detail as desired in the final report.

In certain embodiments, the structured data set may span multiple reference frames with descriptive callouts on each frame. In such data sets, the associated frame images may relay a series of images for the same associated anatomical or pathological feature over multiple time periods or depict before and after images after an intervention.

In certain embodiments, the structured reference frame may map the structured data set to caption boxes or callout boxes linked to certain locations or features shown in the image set. Additional descriptive material may similarly be inserted based on the user's preference, for example, to better describe the anatomical characteristics shown or the pathological characteristics found after medical testing was performed at one or more time points. The caption boxes may be based on drop down selection-based medical information, numeric data, or may permit the user to input free form commentary into the caption box.

In certain embodiments, the structured data set may include medical history specific to the individual patient and use individual reference frames to display this data as caption boxes, callout boxes, or iconography on the structured image set. In certain embodiments, the structured data set may include prognosis information, such as based on an analysis of the structured image set or which combines both the content from historical structured data regarding the patient and structured data newly recorded about the structured image set using the structured reference frame. In certain embodiments, the structured data set may include and display optional treatment recommendations, such as based on the prognosis information or combined with the patient's medical history, current medical status, or projected health status as of the date the structured image set was compiled.

In certain embodiments, data analysis may be performed wholly by a user, automatically, or a combination of both. To facilitate the diagnosis and treatment of the patient, certain embodiments of the present invention may provide access to relevant bodies of information—some examples of which are Clinical Decision Support Guidelines and Acceptable Use Criteria. Advantageously, in certain embodiments, the notifications (e.g., alerts, recommendations, and reminders) that may result from the use of such analytics are seamlessly integrated into the clinical reporting workflow to produce a clinical report.

In certain embodiments, additional hyperlink connections may be inserted into the structured reference frames to connect one structured image set to one or more other structured image sets or another structured reference frame that are connected to associated data, related reports, relevant images or other similar pertinent clinical content to provide further efficient data entry or analysis.

In certain embodiments, a structured image set can be used to automatically trigger the derivation (or retrieval) of analytical results based on recorded data about an anatomical feature or pathology, as well as display the resulting notifications on the associated images. For example, the automatic display of the recommended treatment may be presented based on recorded data from given medical studies combined with data from the patient's electronic medical record. In certain embodiments, by entering a selection of the recommendation notification callout on the image a summary of the associated guideline and the supporting patient data may be displayed.

Certain embodiments of the present invention may allow "hotspots" to be inserted on a reference frame. In the creation of such hotspots, a hyperlink may be initiated when a pointer is positioned on the hyperlinked region indicated on the reference frame. A hotspot may allow initiating the retrieval, review, or recording of data or additional images related to a feature or pathology.

In certain embodiments, the option to create "geometric mapping" of one or more anatomical features or pathologies shown in one or more of the images within a structured reference frame may be available. Geometric mapping of anatomical features or pathology permits points, lines, curves, regions, surfaces, and volumes to be positioned with respect to one or more images in order to track or circumscribe the feature on a reference frame. Through such geometric mapping, the position and shape of features and pathologies may be more accurately defined and modelled. A more detailed spatial mapping between the structured reference and the structured data set describing the characteristics of the given feature may be developed. Use of geometric mapping may be manually controlled or automatically inputted based on user settings. Geometric mapping allows the integration of multiple frames of a given feature or pathology taken from different viewpoints and/or using different imaging techniques at one or more time points. The application of geometric mapping additionally allows for the improved positioning of hyperlinks to data descriptors and additional images. The application of geometric mapping also allows for the calculation of the properties of the feature on an image such as length, area, or volume depending on the geometry of the geometrically mapped feature. Overall, geometric mapping makes enhanced diagnosis and analysis available through the utilization of multiple sources of information and physiological and pathological data.

One of the benefits of the present invention is the introduction of structured image set in which the anatomical features and pathologies depicted in a set of medical images are related to the data descriptors.

Another benefit of the present invention is that certain embodiments permit actual patient imaging to define the bi-directional, spatiotemporal-semantic mapping between the spatiotemporal characteristics of anatomical features and pathologies shown on the images and the data descriptors.

An added benefit of the present invention is that certain embodiments permit the hyperlinking of additional data descriptors or medical images to a primary image or set of images depicting the patient's anatomy and/or pathology.

A further benefit of the present invention is that certain embodiments permit incorporation of geometric mapping that may provide qualitative information regarding the shape's length, area, volume, etc. The use of geometric mapping may also provide the benefit of a reconstructed configuration of multiple images taken from different perspectives or from multiple time points to demonstrate the three-dimensional shape and/or change in the anatomical features over time.

Another benefit of certain embodiments of the present invention is the improved positioning of data descriptors on the images of the actual anatomy that are the subject of the report narrative.

An additional benefit of certain embodiments of the present invention is the automation of geometric mapping of one or more images with the option of manual intervention to depict the anatomical feature of interest.

Another benefit of certain embodiments of the present invention is that they may permit the incorporation of multiple images from multiple imaging techniques into the same structured image set, such as to describe a patient's anatomical and physiological/pathological conditions.

Another benefit of certain embodiments of the present invention is that they may facilitate the analysis of a given geometric mapped region based on known medical procedures combined with the patient's medical history to create a treatment option plan for the individual's healthcare needs.

Another benefit of the present invention is that certain embodiments facilitate the incorporation of additional commentary notes in the given report through audio or written communication.

Another benefit of the present invention is that certain embodiments facilitate the creation of the structured image sets and input of the reference frames, geometrical mapping, data descriptors and associated hyperlinks to additional data descriptors and relevant additional images through voice or audio control.

In certain advantageous embodiments, the system and methods provides a means to present structured image sets that may be produced for target audiences. For example, while a patient's medical images provide a "gold standard" perspective on a patient's anatomy and pathology, medical images may not be easily understood by physicians, patients, or family members lacking expertise in interpreting a particular medical imaging modality. Augmenting medical images with relevant material prepared by an expert physician may assist in the interpretation and use of medical images by non-experts. The system provides a means to present data to target audiences, whether the audience is specialized medical doctors or the patient or family member not equipped with medical training to read complex medical images, reports or data charts.

The invention and its attributes and advantages will be further understood and appreciated with reference to the detailed description below of presently contemplated embodiments, taken in conjunction with the accompanying drawings.

BRIEF DESCRIPTION OF THE DRAWINGS

Embodiments are illustrated by way of example and not limitation in the figures in the accompanying drawings, in which like references indicate similar elements and in which.

DETAILED DESCRIPTION OF EMBODIMENTS OF THE INVENTION

Figure 1:
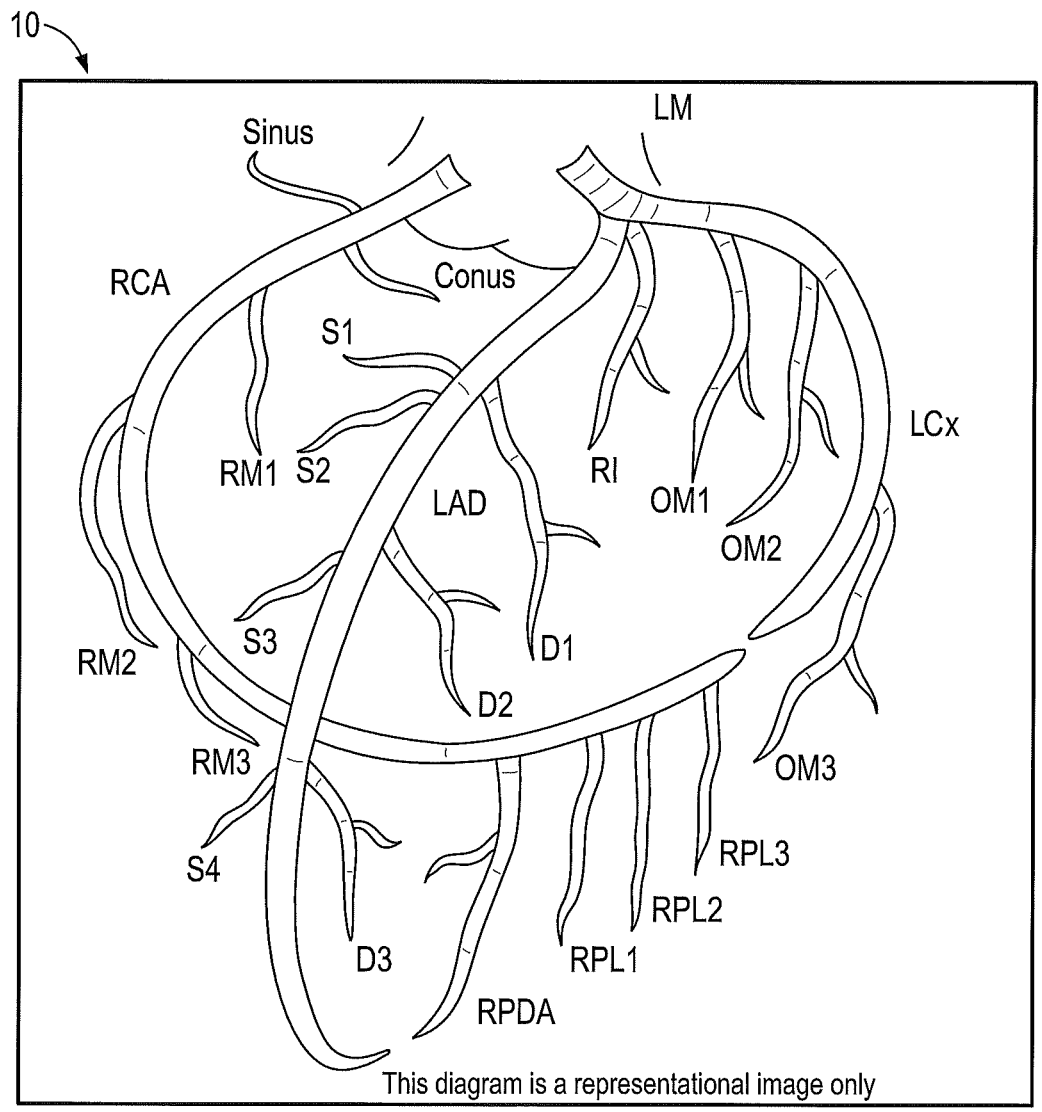
FIG. 1 illustrates a prior art example of an anatomical cartoon line drawing and an associated structured data set.
Figure 2:
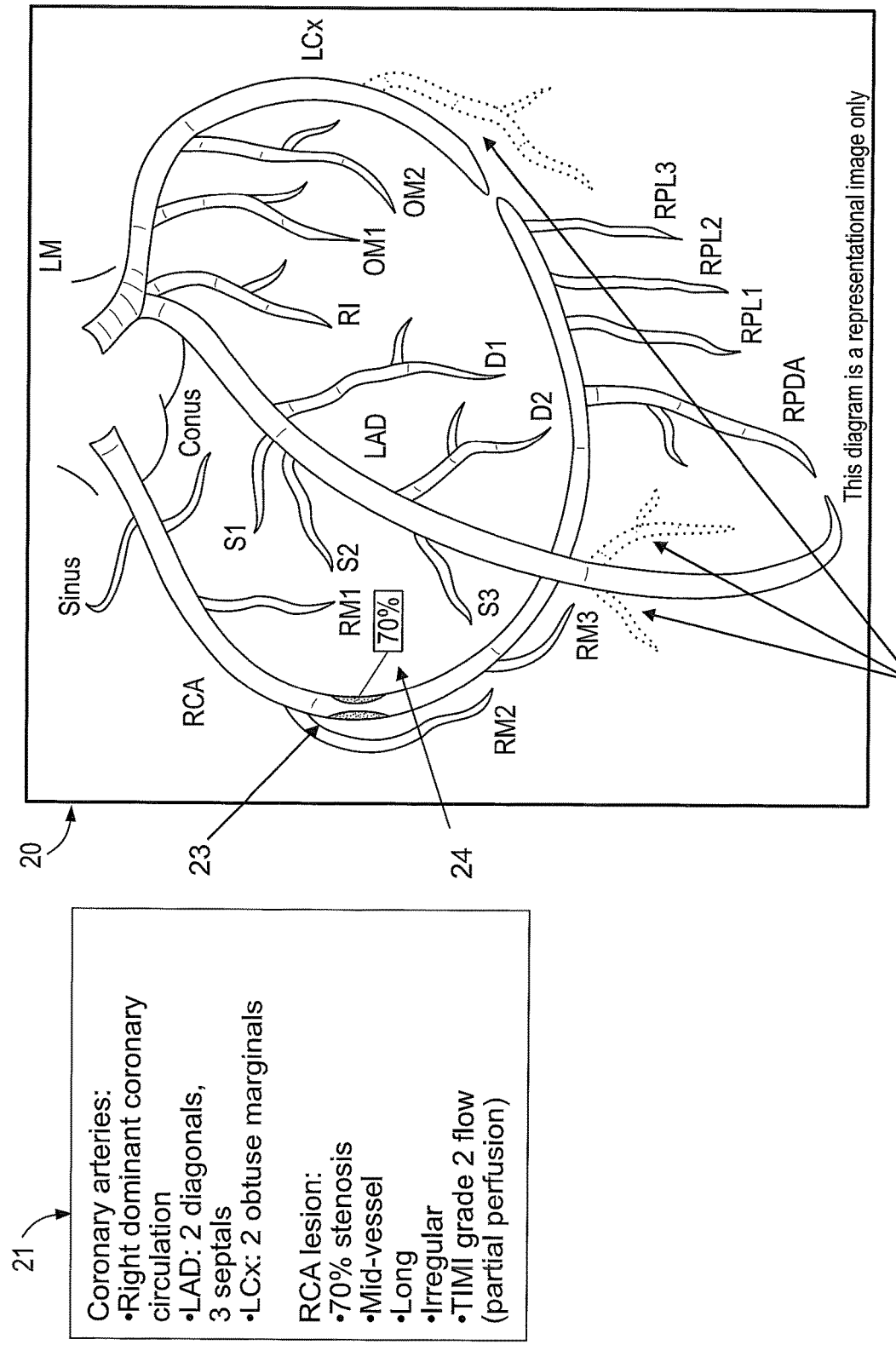
FIG. 2 illustrates the prior art example of the drawing shown in FIG. 1 in which the drawing has been modified based on a recorded structured data.
Figure 3:
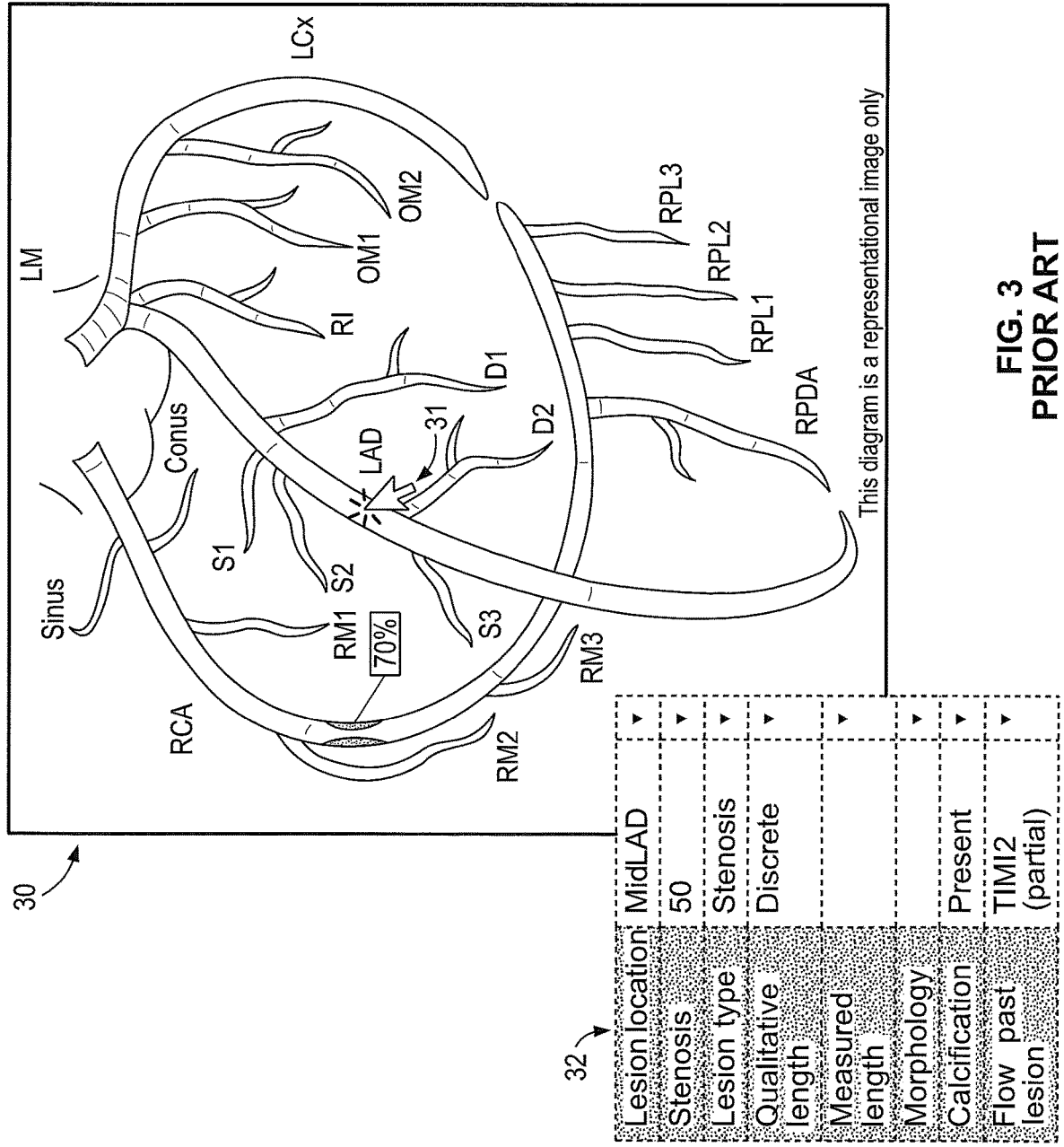
FIG. 3 illustrates the prior art example of the drawing shown in FIG. 1 and FIG. 2 that includes a data entry form for recording data about a selected anatomical feature or pathology and a narrative report that includes the data entered in the form.
Figure 4:
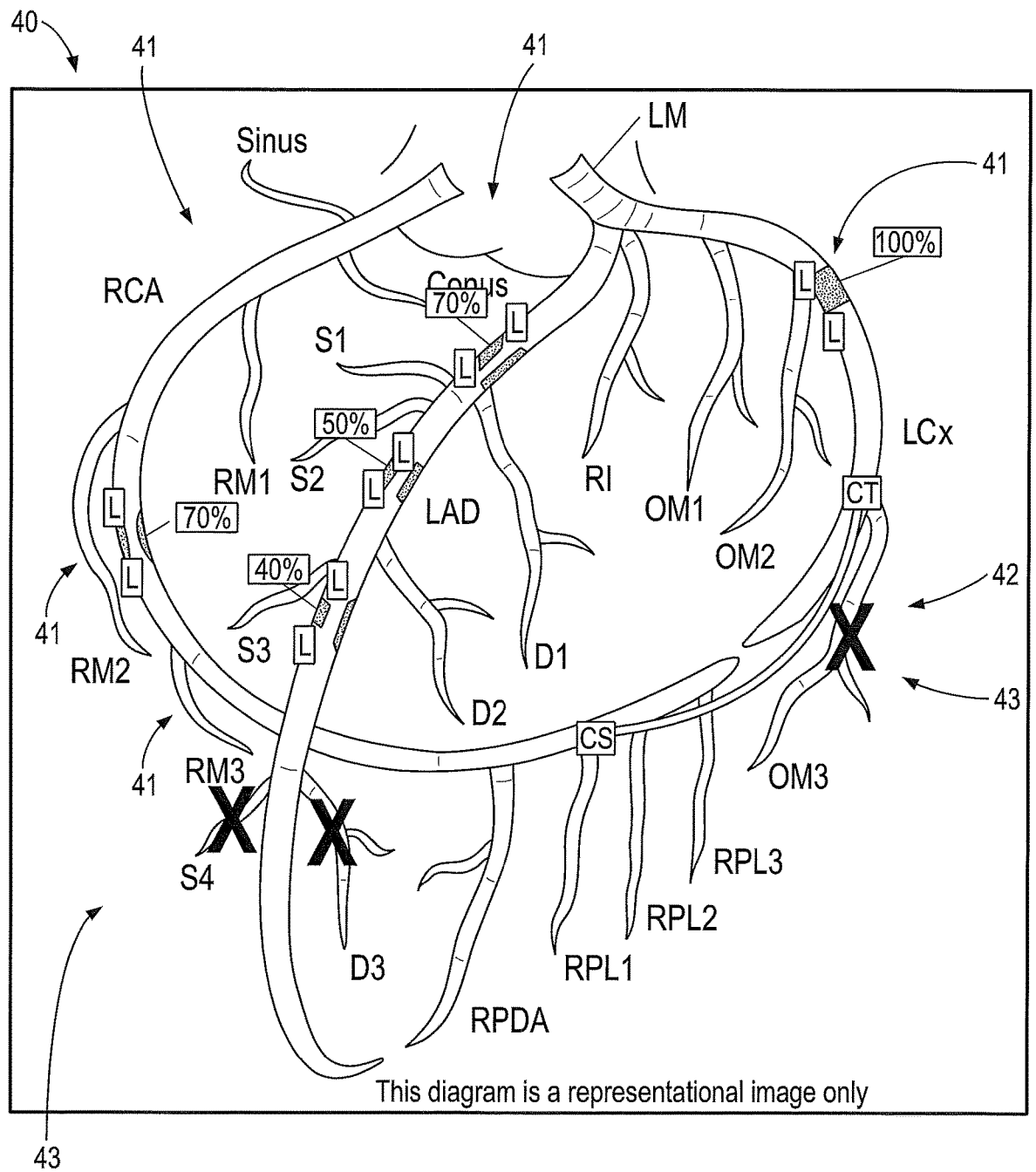
FIG. 4 illustrates the prior art example of the drawing shown in FIG. 1, FIG. 2, and FIG. 3 that contains graphical components derived from anatomical features and pathologies.
Figure 5:
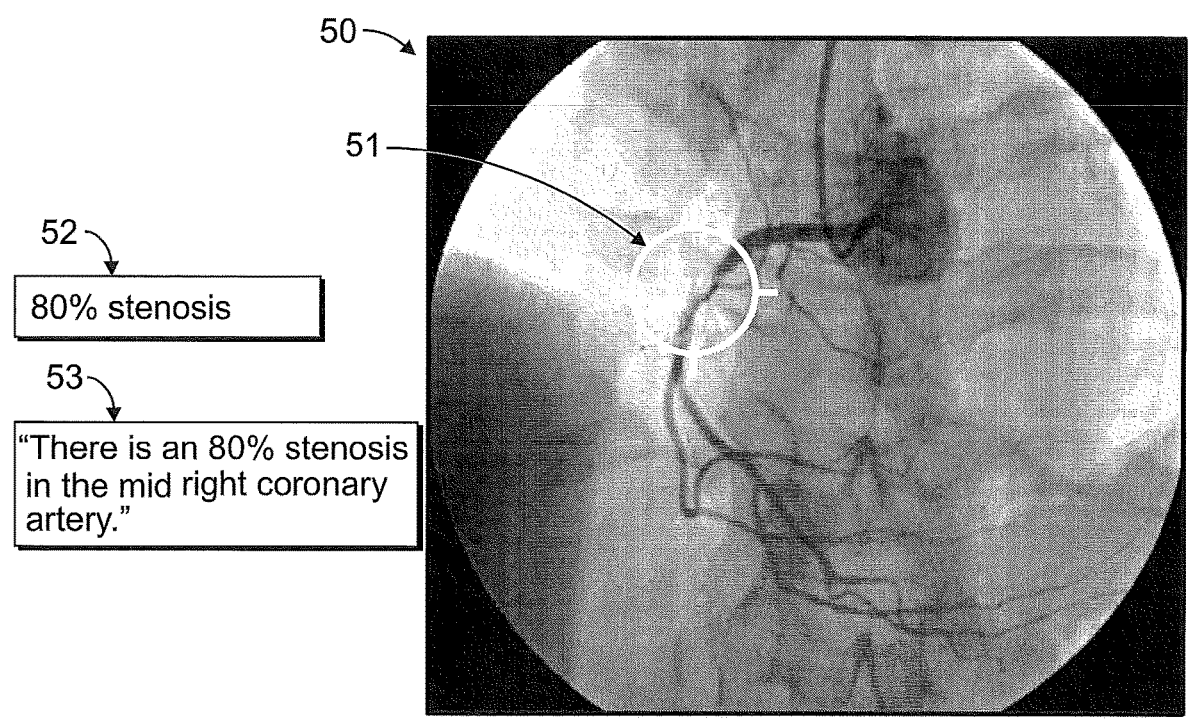
FIG. 5 illustrates a prior art example of a measurement and free-text annotation associated with a pixel region ("Region of Interest") in a medical image.

FIG. 1 through FIG. 4 illustrate a certain prior art example of a reporting system that includes a simple diagram that utilizes an anatomical cartoon and other elements described above. FIG. 5 illustrates a certain prior art example of a reporting system that includes associating a measurement or free-text annotation with a pixel region on a medical image. FIG. 6 through FIG. 28 illustrate embodiments of a system and methods according to the present invention.

Figure 6:
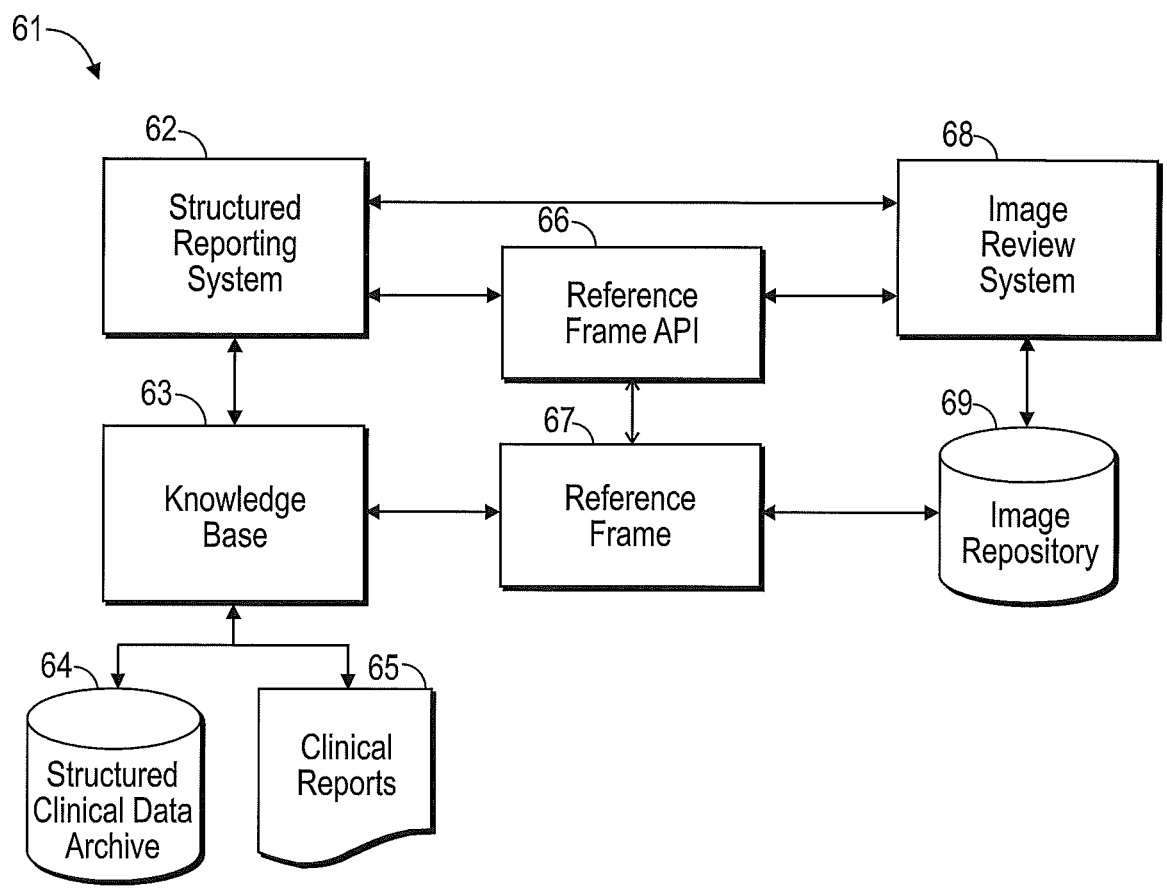
FIG. 6 is a schematic diagram illustrating the operation of one preferred embodiment of the present invention.

FIG. 6 illustrates one of the preferred embodiments of the present invention by which a clinical report may be generated. In the embodiment of the system 61 illustrated in FIG. 6, the structured reporting system 62 interoperates with an image review system 68. The image review system 68 may retrieve one or more images from an image repository 69 (for example, a DICOM archive) for display, review, measurement, and/or annotation. While in the preferred embodiment of the proposed invention shown in FIG. 6, the structured reporting system 62 and the image review system 68 are separate interoperating systems, another preferred embodiment provides the structured reporting and the image review functions as subsystem components of a single integrated system.

In the system 61 illustrated in FIG. 6, the reference frame API 66 may facilitate the bi-directional association (such association also termed for purposes of this application, "mapping") between the spatiotemporal characteristics of the anatomical features and pathologies shown on one or more of the images selected from the image repository 69 and the information that may describe these features and pathologies that may be provided through the knowledge base 63 (such information also termed for purposes of this application, "structured data set"). The reference frame 67 of the embodiment illustrated in FIG. 6 may be used to associate:

an anatomical feature or pathology with one or more structured image objects (e.g., sets of points, Regions of Interest or "ROIs", lines, curves, regions, shells, or volumes) that specify a feature or pathology's spatial characteristics (e.g., position, length, diameter, contour, area, shape, or volume) as it appears on one or more images from the image repository 69; and descriptive elements (e.g., lines, curves, shapes, regions, text, or fills) that are used to provide the descriptive iconography, drawings, callouts, and captions that depict or describe a feature or pathology as an overlay or modification of the one or more images from the image repository 69.

In the Illustrated embodiment of the system 61, the interaction between the structured reporting system 62 and the image review system 68, and that which results from that interaction may be facilitated using the reference frame applications program interface ("API") 66.

The knowledge base 63 may be used to provide access to information about a specific clinical topic stored in a structured clinical data archive 64 and may permit the structured reporting system 62 to be used to support the creation of clinical reports 65 based on the recorded structured clinical data from the archive 64 including: the generation and display of data entry forms, diagrams, or other user interface (UI) elements; the recording and storage of data; the generation of narrative text, tables, diagrams, or other material from recorded data; and the presentation of recorded data for review or revision through a screen display or in a clinical report.

Figure 7:
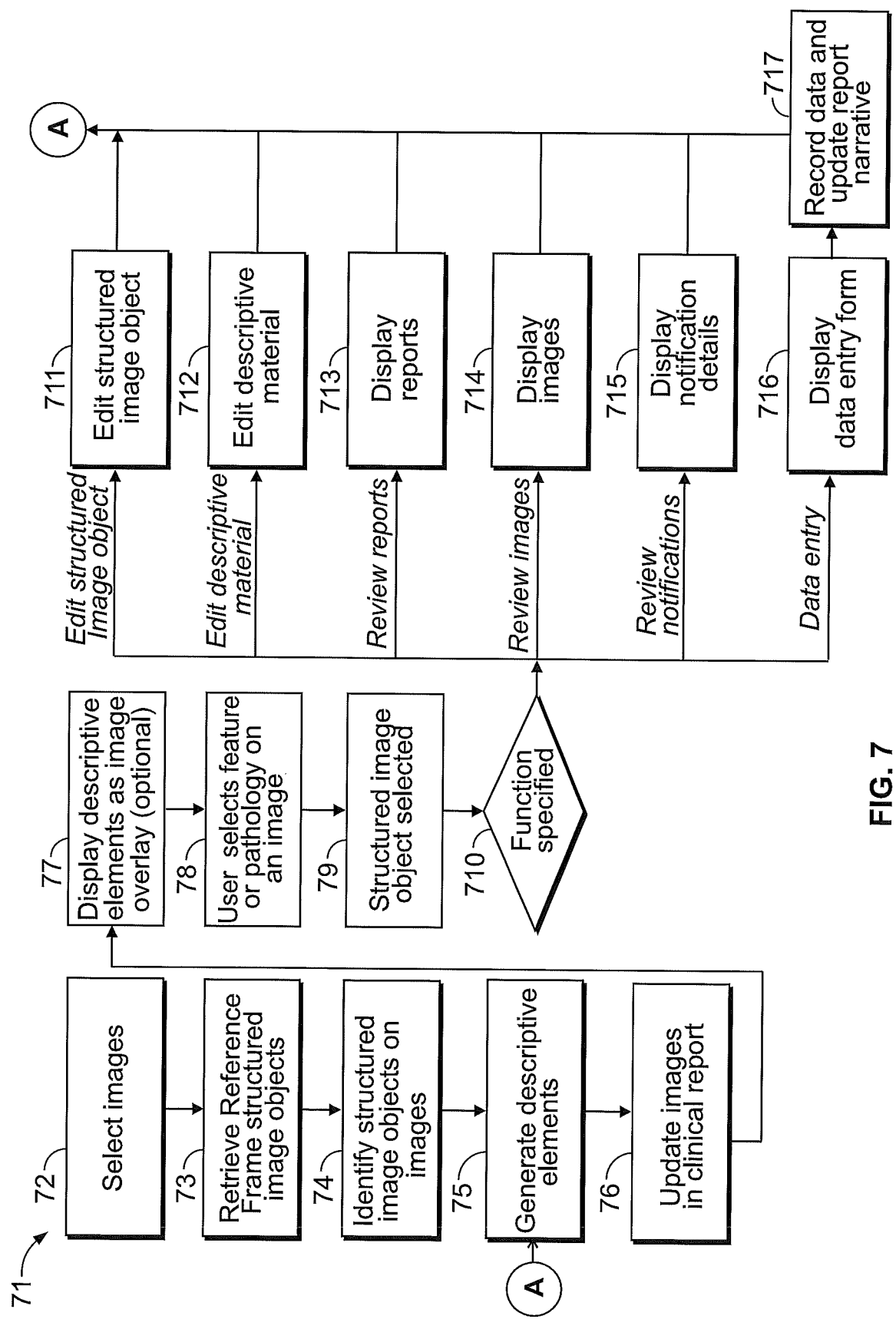
FIG. 7 is a flow chart illustrating the operation of one preferred embodiment of the present invention.

FIG. 7 illustrates further details of a system 71 by which that the preferred embodiment of the proposed invention shown in FIG. 6 may be used to instantiate and permit the use of a reference frame to perform various tasks in order to prepare a clinical report which may include one or more images. FIG. 8A, FIG. 8B, FIG. 8C, FIG. 8D, and FIG. 9 provide some examples of coronary images that processed through the use of the embodiments of the invention shown in FIG. 6 and FIG. 7.

Figure 8B:
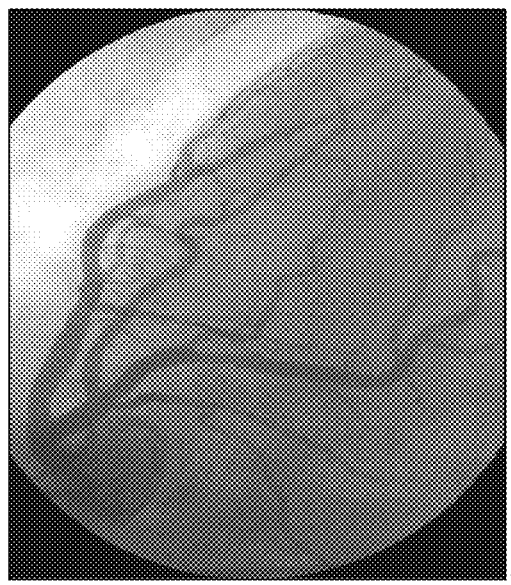
FIG. 8B illustrates another example of a medical image that may be processed through the use of one embodiment of the present invention.
Figure 8D:
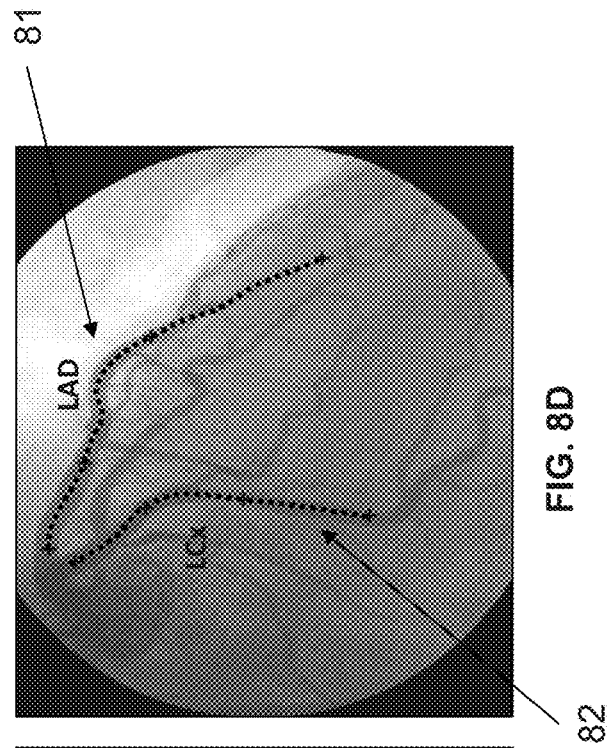
FIG. 8D illustrates an example of a medical image that is processed through the use of one embodiment of the present invention.
Figure 8A:
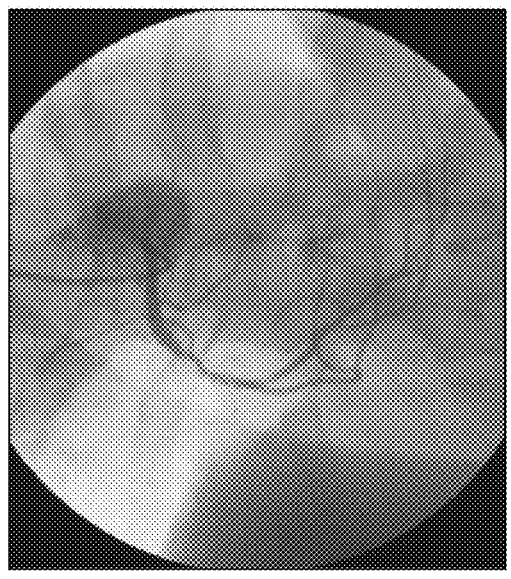
FIG. 8A illustrates an example of a medical image that may be processed through the use of one embodiment of the present invention.

As a first step in the use of the embodiment of the system 71 illustrated in FIG. 7, a health care worker—such as a physician or a technician—may select one or a set of images 72 to use to prepare a clinical report. FIG. 8A and FIG. 8B provide examples of two related coronary images that a health care worker may select for processing so that a clinical report may be prepared that includes one or more of these images, the two related images being actual coronary images taken of a patient.

Through the use of the image review system 68 and the reference frame API 66, reference frame structured image objects may be retrieved 73 for association with the selected images based on, for example, the imaging procedure being performed (e.g., modality, anatomy), the images themselves (e.g., view, timing), and/or other input from the user.

Figure 8C:
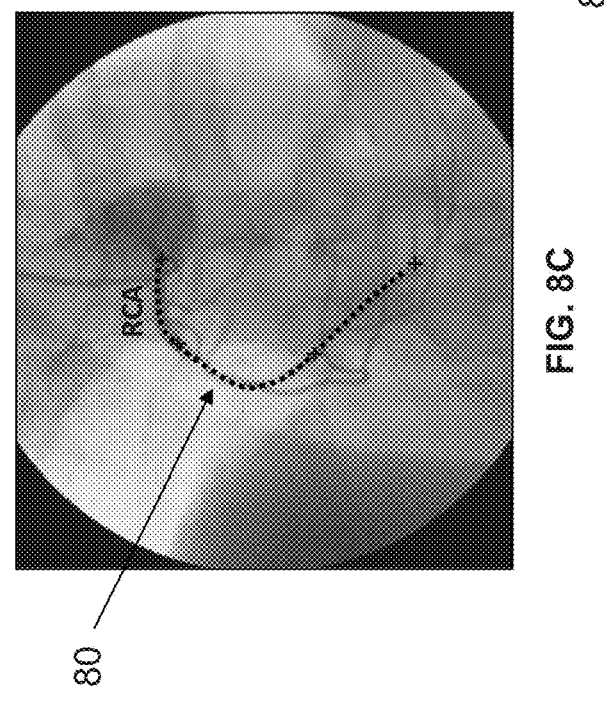
FIG. 8C illustrates an example of a medical image that is processed through the use of one embodiment of the present invention.

In the embodiment of the system 71 illustrated in FIG. 7, a health care worker may identify whether and where an anatomical feature and pathology occurs on an image and choose which one or more of the retrieved structured image objects to associate with the feature or pathology on the images 74. A user may use the reference frame API 66 to update the reference frame 67 with the instantiated structured image objects. In one preferred embodiment of the present invention, a user (e.g., a health care worker) may position and align a list of anatomical features and pathologies with the corresponding image. Questions directed to features or pathologies that do not occur on the image can be reserved in the "identification by positioning" step 74. Alternate embodiments of the proposed invention may use procedures that are manual, semi-automated, or fully-automated, including procedures in which user actions are prompted (system-directed) or unprompted (user-directed), to accomplish the identification by positioning step 74. FIG. 8C and FIG. 8D show each of the reference frame images selected by the health care worker, FIG. 8A and FIG. 8B, respectively, in which a reference frame was used to position structured image objects (a contrasting dashed line with a "+" sign at each line termini) corresponding to the right coronary artery (RCA) 80, left anterior descending artery (LAD) 81, and left circumflex artery (LCx) 82 onto the selected images.

The embodiment of the system 71 illustrated in FIG. 7 then may be used to generate one or more descriptive elements (e.g., iconography, drawings, callouts, captions) 75 based on recorded clinical data for each structured image object, using the reference frame to define the position and extent of each descriptive element. These descriptive elements may be applied to the images so that they may be used in the clinical report 76. One such preferred embodiment of the structured reporting system may automatically generate such descriptive elements.

Figure 9:
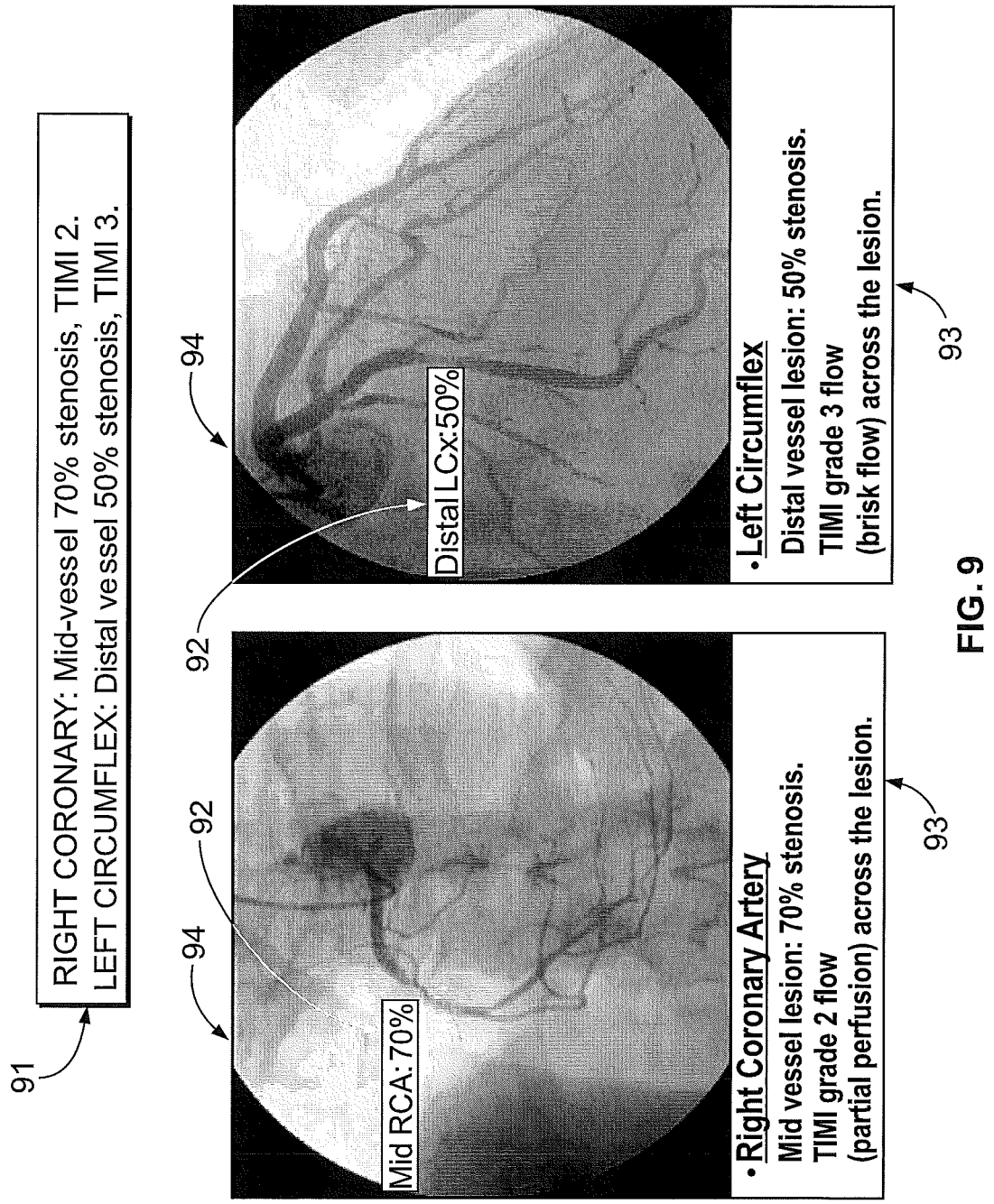
FIG. 9 illustrates the medical images processed through the use of one embodiment of the present invention.

The image review system 68 may be used with the reference frame API 66 to retrieve the reference frame 67, including the structured image objects and the associated descriptive elements, in order to overlay one or more of the selected images with the appropriate descriptive elements 77. FIG. 9 shows the coronary images also shown in FIG. 8A and FIG. 8B that include a pair of descriptive callouts 92 and captions 93 in which data generated through the use of a hemodynamics system-generated data shown in data box 91 is imported on the image using the reference frame (illustrated in FIG. 9 by the number 94 and a line with an arrowhead).

Embodiments of the present invention may be used to process the selected one or more images such that a user (e.g., a health care worker or another) may select (e.g., by "clicking" on) an anatomical feature or pathology shown in the one or more of the selected images 78 and obtain additional information or data. The image review component 68 of the system 71 may use the reference frame 67 to associate the location of the selection action (e.g., the "click") to, for example, the associated structured image object 79 and the associated knowledge base element(s) 63, clinical structured data set 64, and/or clinical reports 65.

The health care worker seeking to prepare a clinical report may then perform one or more of the following functions on the anatomical feature or pathology referenced by the selected structured image object 710:

Edit the position or extent of the structured image object to make it conform more accurately to the associated feature or pathology 711.

Edit the position or content of descriptive material related to the selected feature or pathology, including removing it entirely 712.

Display, such as for review, clinical or other reports related to the selected feature or pathology, including reports from imaging studies from different modalities and procedures, as well as clinical reports from the patient's electronic medical record ("EMR") 713.

Display, such as for review, one or more medical images related to the selected feature or pathology, including imaging studies from different modalities and procedures 714.

Display, such as for review, information related to displayed notifications (e.g., alerts, warnings, reminders), including notification details and explanations 715.

Display, such as for review, a data entry form for recording additional data about the selected feature or pathology 716. The Reference Frame API 66 can be used to retrieve the corresponding data fields for display within the Image Review System 68. The Structured Reporting System 62 can be synchronized to the selected feature or pathology. A user (e.g., a health care worker) may also record data using a data entry form, keyboard, voice input, or on-screen measurement tools depending on the option chosen by the user of the system 71.

The system 71 may then be used to pass recorded data to the structured reporting system 62, and a report narrative and descriptive elements generated that can be used in a procedural report, structured images, and the patient's electronic medical record 717.

FIG. 10 through FIG. 28 provide additional information regarding embodiments of the system 71 according to the present invention.

Figure 10:
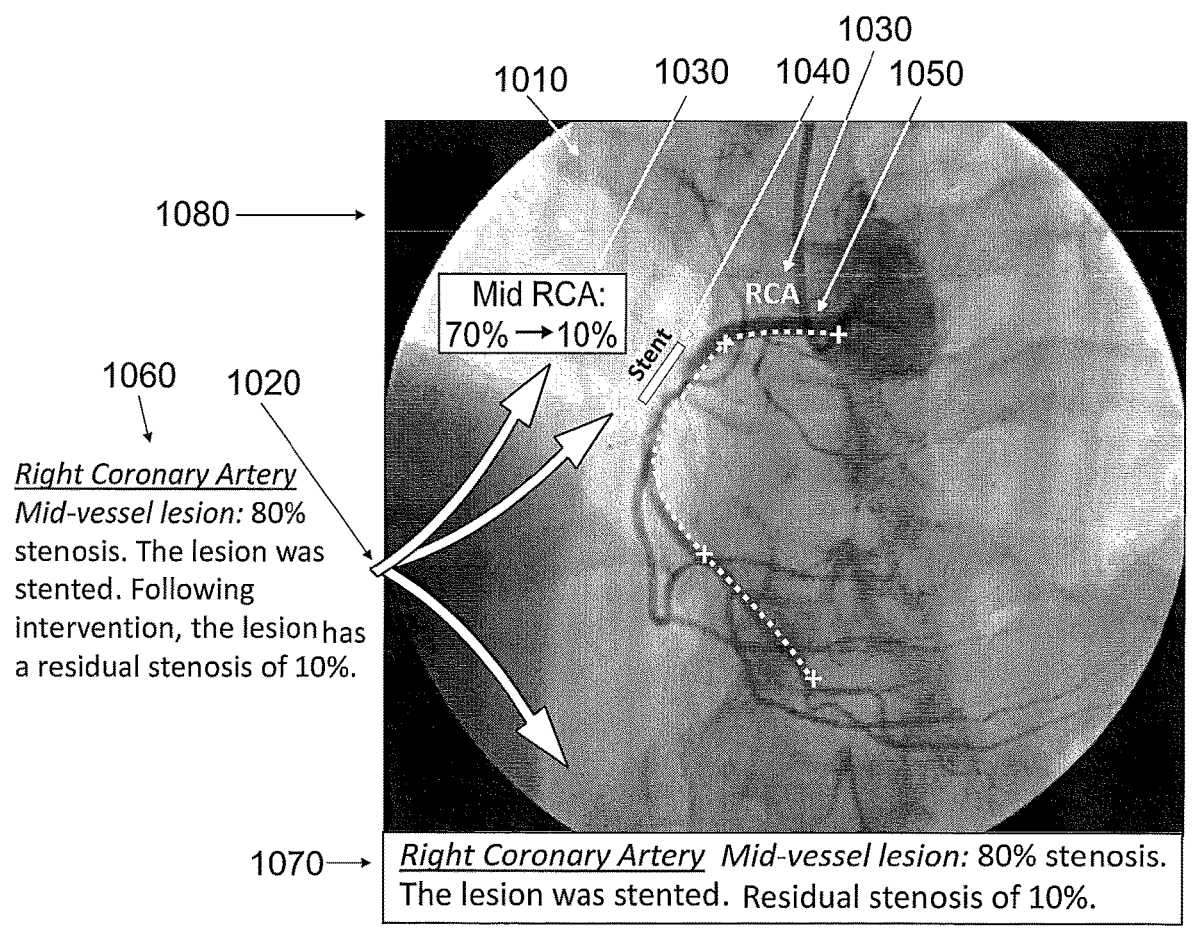
FIG. 10 illustrates an example of a medical image processed through the use of one embodiment of the present invention.

FIG. 10 illustrates an example of the use of an embodiment of the invention to associate information and data (the "association" illustrated in FIG. 10 as a set of arrows 1020) through a reference frame with an image taken of a patient 1010 to produce a structured image 1080.

In this embodiment of the invention, the reference frame 1020 is used to automatically associate the patient image 1010 with information provided in the recorded structured data component 1060 and to generate data information components (callouts, icons, captions, etc.) on the image based on the recorded data.

Advantageously, certain embodiments of the system may include one or more data information components 1030 that provide abbreviated information regarding one or more anatomical features under consideration, such information components including those termed a "callout" for purposes of this application. The structured image 1080 shown in FIG. 10 includes a data information component 1030 that identifies through an acronym "RCA" that the user is viewing an image showing the right coronary artery and information from the recorded structured data 1060 but in abbreviated form regarding the anatomical feature under consideration—that is, information regarding how the stenosis of the imaged artery changed following surgical intervention ("70%->10%").

Advantageously, certain embodiments of the system 71 may offer to a user one or more icons that may be of relevance to that which is the subject of the study and permit the user to select and position the one or more icons in association with one or more of the selected images taken of a patient. The structured image 1080 shown in FIG. 10 includes an icon 1040—in this example, an elongated rectangular shape that symbolizes a stent and informs the viewer that a stent was positioned in the artery and the location of the stent. Such an icon may graphically represent that which is expressed in words in the recorded structured data 1060. In this case, the stent icon represents the words "The lesion was stented." Such as icon may be accompanied by one or more numbers, alphabets, words, or other symbols to provide confirming or new information. To illustrate, in FIG. 10, the icon symbol is accompanied by the word "stent".

Embodiments of the system 71 may permit a user to identify, emphasize, or highlight an anatomical feature by using one or more structured image objects—also termed "graphical components" for purposes of this application—to develop a graphical structure. The embodiment shown in FIG. 10 shows a graphical structure 1050 developed by a user from two graphical components—a dashed line and "+" signs positioned at the termini of the line—to produce a line design and its position to illustrate the path of the artery that is the subject of the study for the selected image.

Advantageously, certain embodiments of the present invention may include an additional information component—a caption 1070—that adds to, summarizes, or highlights information regarding the structural image 1080. The embodiment of the system 71 from which the structured image 1080 shown in FIG. 10 was produced includes an information component—caption 1070—that in this example provides a summary of the information in the associated structured data set 1060.

Embodiments of the system 71 may be used to map structured data about the anatomy and/or pathologies recorded independently of an image or data entered for the one or more selected images to produce or augment the associated structured image. With respect to the image shown in FIG. 10, the narrative 1060 provides information recorded about a mid-RCA stenosis and its treatment and presents in more complete form the abbreviated information presented in the data information components 1030, graphical data component 1040, graphical structure 1050, and a data caption 1070—that is, the stenosis data entered for the imaged artery and the result of the surgical intervention. As with the components 1030, 1040, 1050, and 1070, the narrative 1060 may be automatically generated from the structured knowledge base 63 based on the structured data set 64.

Embodiments of the system 61, 71 may also include additional components by which information may be entered with respect to one or more images. Depending on the embodiment of the invention, the displayed information and graphical data components may be inserted and positioned as desired manually or inserted, in part or wholly, through automation features. Depending on the embodiment of the invention, the displayed information and graphical data components that may be inserted and positioned on a selected image 1010 by a user (such as a health care worker) doing the study of the selected anatomical feature or pathology may be subsequently manipulated—for example, by the reporting or referring physician—as desired. For example, a reporting or referring physician may wish to select only certain of the displayed information and graphical data components shown through the structured image 1080 for purposes of presenting the results of the study to a patient or patient representative. The information that is not chosen by the physician to present to the patient may be, for example, historical data with which the patient is already familiar.

Embodiments of the system 71 may allow a user to modify the position, nature, or content of the displayed information or graphical data components and, in so doing, to modify the associated structured data set. For example, a user may wish to change the information displayed in the data information component 1030—"10%" to "5%", whereupon the system 71 would modify the information in the recorded structured data component 1060 which, in turn, would modify the image caption 1070 to reflect the new residual stenosis value, —"Residual stenosis of 5%". As another example, a user may describe the diameter and length of the stent depicted as an icon 1040 to be 5 mm in diameter and 25 mm in length, whereupon the system 71 would modify the associated structured data set 1060 and caption 1070 to describe also the new diameter and length information, as in "The lesion was stented with a 5 mm (D)×25 mm (L) stent." Additionally, the length, diameter, shape, and other geometric characteristics of the structured image object—the "dashed" line—tracking the RCA vessel 1050 may be modified or the position of the stenotic lesion adjusted, whereupon the system 71 would modify the associated structured data set 1060 to reflect these changes.

Figure 11:
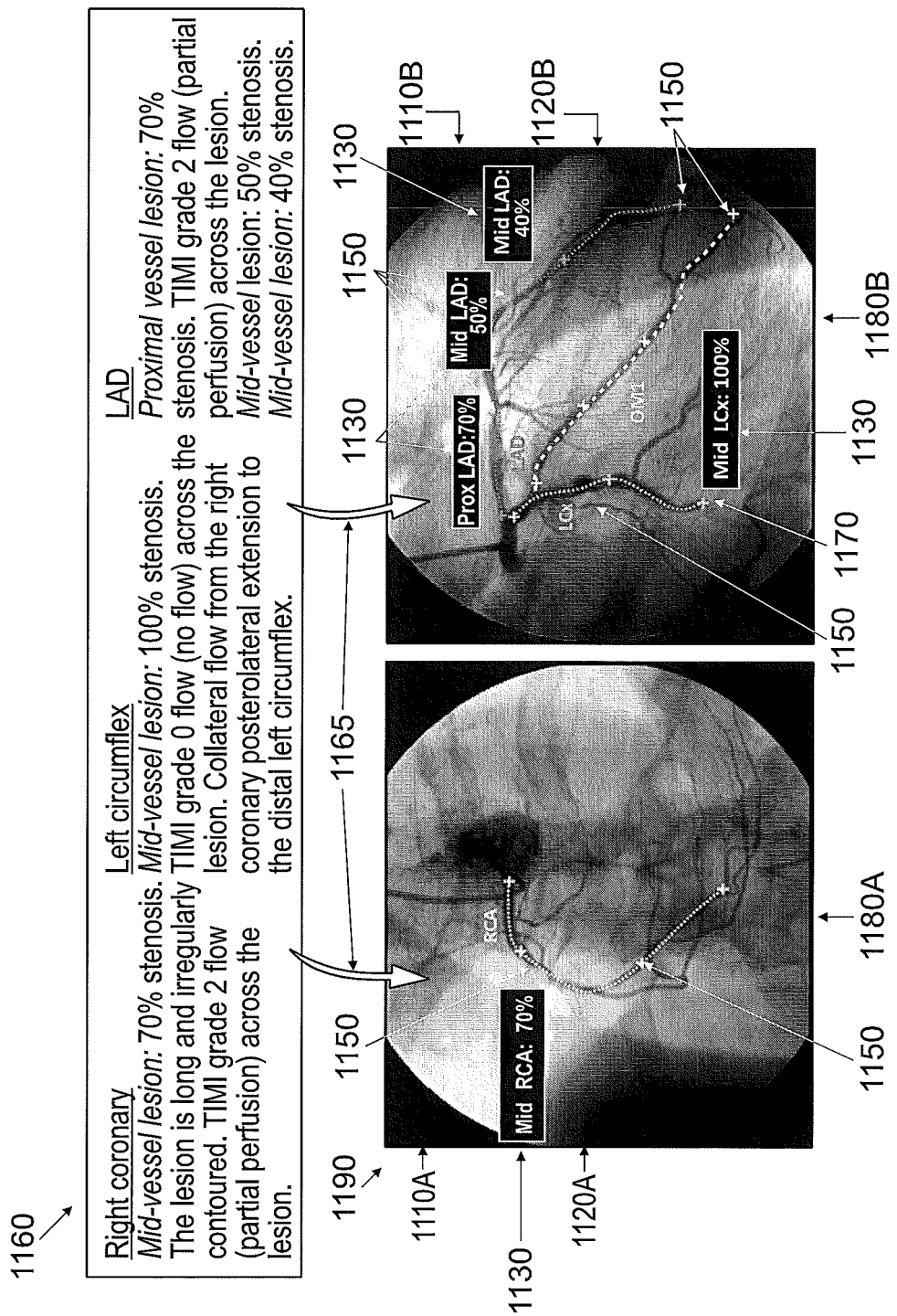
FIG. 11 illustrates an example of a medical image processed through the use of one embodiment of the present invention.

FIG. 11 illustrates an embodiment of the system in which a wider range of information may be presented for a patient through the use of multiple images taken of the patient 1110A, 1110B, each is augmented by associating or mapping recorded structured data 1160 using a reference frame (denoted by the arrows 1165) to produce a structured image set 1190. The structured image set 1190 shown in FIG. 11 includes a structured image 1180A formed from an image 1110A that was taken from that same view from which the image 1010 shown in FIG. 10 was taken (but here of a different patient) and a structured image 1180B formed from an image 1110B taken from a different view of the same patient from which image 1110A was produced. The presentation of a plurality of images of a patient and information and data regarding those images and the patient viewable as a structured image set 1190 and on a single screen advantageously places the information and data efficiently in a greater spatiotemporal context.

Each of the structured images 1180A, 1180B shown in FIG. 11 includes graphical structures 1150 developed and positioned by a user to track the course of various coronary arteries. In structured image 1180A, the path of the right coronary artery is identified with a data information component 1030—that is, the acronym "RCA"- and graphical structures 1050, each formed from dots and "+" signs. In structured image 1180B, the paths of three blood vessels are separately identified with data information components 1030—that is, "LCx", "OM1", and "LAD"—and graphical structures 1050 formed from dots and "+" signs and dashes and "+" signs.

The structured images 1180A, 1180B shown in FIG. 11 include data information components 1130 derived from the associated structured data 1160, each of which is presented as a callout containing abbreviated information regarding the anatomical features under consideration—that is, information regarding the percentage of the narrowing or stenosis that is found in each of certain locations of the blood vessels, where each data information component 1030 is positioned adjacent to the image 1170 of the blood vessel.

The embodiment of the invention from which the structured image set 1190 was produced allows a user also to map structured data about the anatomy and/or pathologies recorded independently of an image or data recorded about the selected images to produce or augment the associated structured image. With respect to the images shown in FIG. 11, the narrative in the recorded structured data component 1160 provides information recorded about the displayed coronary stenoses and their treatment and presents this information in more complete form than the abbreviated information presented in the data information components 1130 and graphical structures 1150—that is, the stenosis data entered for the imaged blood vessels. As with the components 1130 and 1150, the narrative shown in the recorded structured data component 1160 may be automatically generated from the structured knowledge base 63 based on the structured data set 64.

Figure 12B:
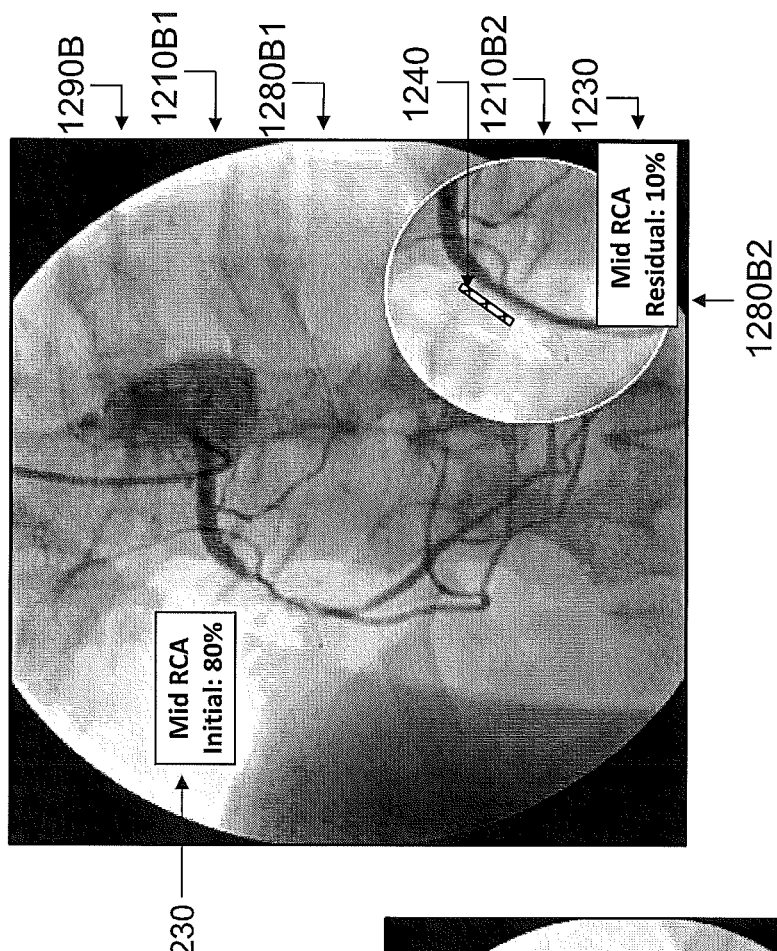
FIG. 12B illustrates another example of a structured image set prepared through the use of one embodiment of the present invention.
Figure 12A:
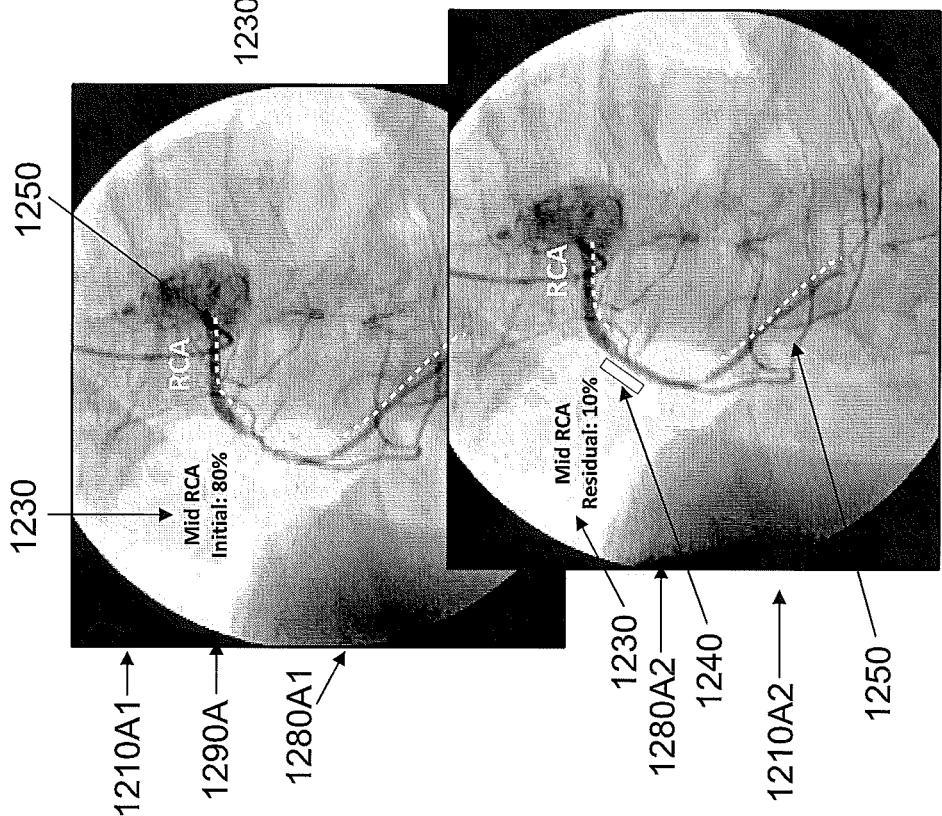
FIG. 12A illustrates an example of a structured image set prepared through the use of one embodiment of the present invention.

FIG. 12A and FIG. 12B illustrate examples of the different structured image sets that may be developed and presented through the use of certain embodiments of the present invention.

The structured image set 1290A shown in FIG. 12A is formed from a structured image 1280A1 juxtaposed relative to structured image 1280A2. Structured image 1280A1 is formed from an image 1210A1 taken from a certain view of a patient that includes a graphical structure 1250 showing the path of the right coronary artery and a data information component 1230 that provides abbreviated information regarding the amount of stenosis of the artery that the patient had at one time prior to surgical intervention. Structured image 1280A2 is formed from an image 1210A2 taken from the same view as that from which the image 1210A1 was taken but after a surgical intervention—the placement of a stent in the artery. Structured image 1280A2 includes a graphical structure 1250 showing the path of the artery, a data information component 1230 that provides abbreviated data regarding the effect of the surgical intervention, and an icon 1240—in this example, a rectangular shape informing the viewer that a stent was positioned in the artery and the location of the position of the stent. The juxtaposition of structured image 1280A2 "forward from" or "on top" of structured image 1280A1 to form the structured image set 1290A implicitly provides to the viewer the most recent information for the patient in a forward position—that is, the closest to the viewer—while the older information appears as a partial image 1280A1 that may be brought forward by "selecting" (e.g., "clicking" on) it.

FIG. 12B shows a different presentation of a structured image set 1290B. Structured image set 1290B is formed from structured image 1210B1 and structured image 1210B2. Structured image 1210B1 is taken from a view of the patient identical to that from which the structured image 1210A1 was taken—that includes a data information component 1230 providing information regarding the amount of stenosis found in this patient's artery but without a graphical structure 1250. Structured image 1210B2 is a reduced portion of a complete image and includes a data information component 1230 and an icon 1240 informing the viewer the presence and location of a stent positioned in this blood vessel. Certain embodiments of the present invention permit the structured image set 1290B to be produced automatically by a user from the image content and the descriptive material provided in the structured image set 1290A.

Figures 13A, 13B:
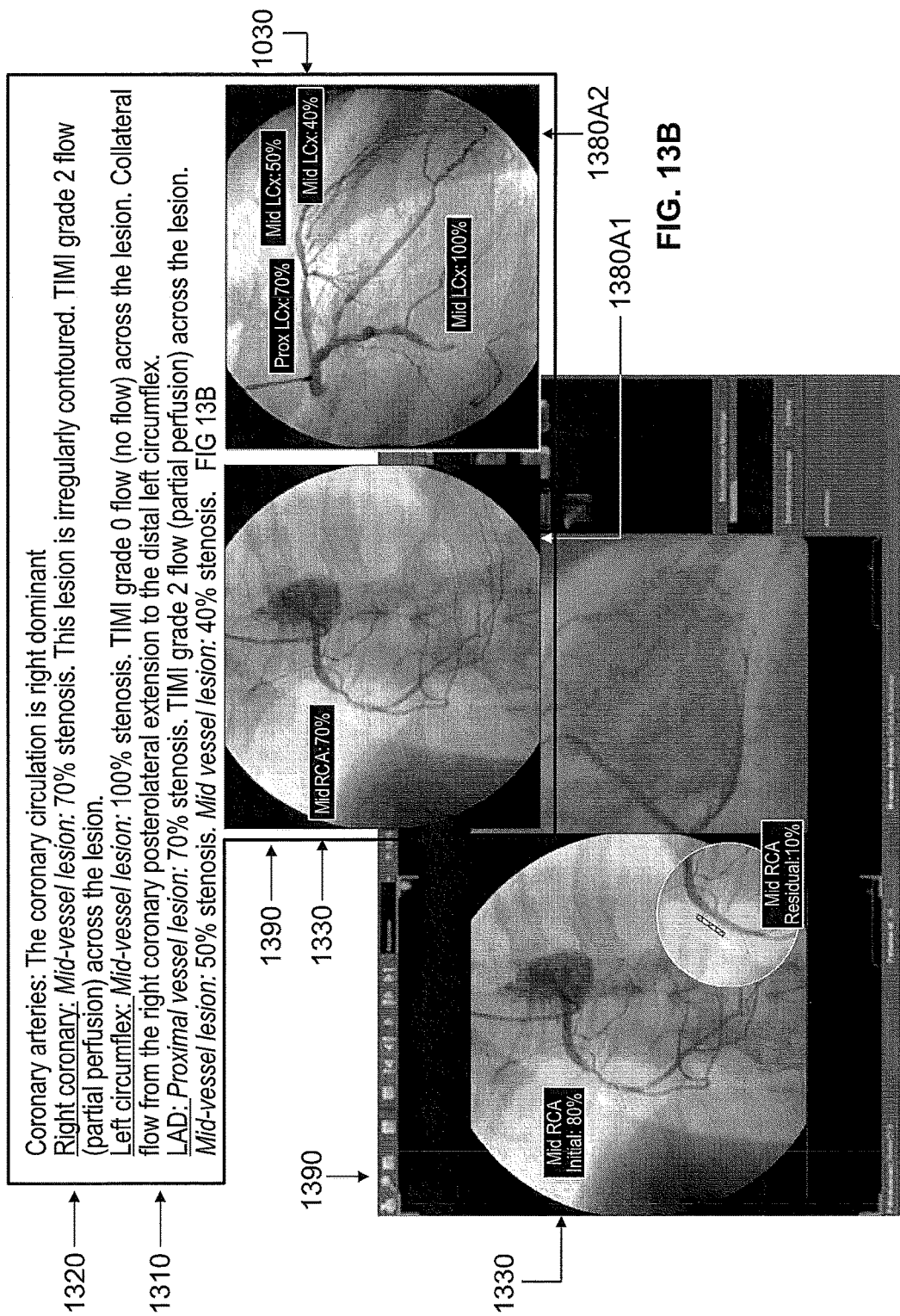
FIG. 13A illustrates an example of the context in which a structured image set prepared through the use of one embodiment of the present invention may be presented to a user.
FIG. 13B illustrates another example of the context in which a structured image set prepared through the use of one embodiment of the present invention may be presented to a user.

FIG. 13A and FIG. 13B illustrate one of the many contexts in which a structured image set 1390—formed from images 1380A1, 1380A2—may be presented to a user, such as a health care worker. FIG. 13A shows an embodiment of the invention through the use of which the structured image set 1390 may be presented to a user on a display device thereby allowing the user to review the images and the information included in the images. Similar to the set 1290B shown in FIG. 12B, FIG. 13A includes a data information component 1330 and an icon 1340. FIG. 13B shows an embodiment of the invention through the use of which the structured image set 1390 may be integrated into and presented as all or part of a clinical report 1310. The embodiment of the clinical report shown in FIG. 13B includes a narrative element 1320, that may provide more information than the abbreviated information presented in the data information components 1330 positioned in each of the images, 1380A1, 1380A2 from which the set 1390 is formed.

Figure 14:
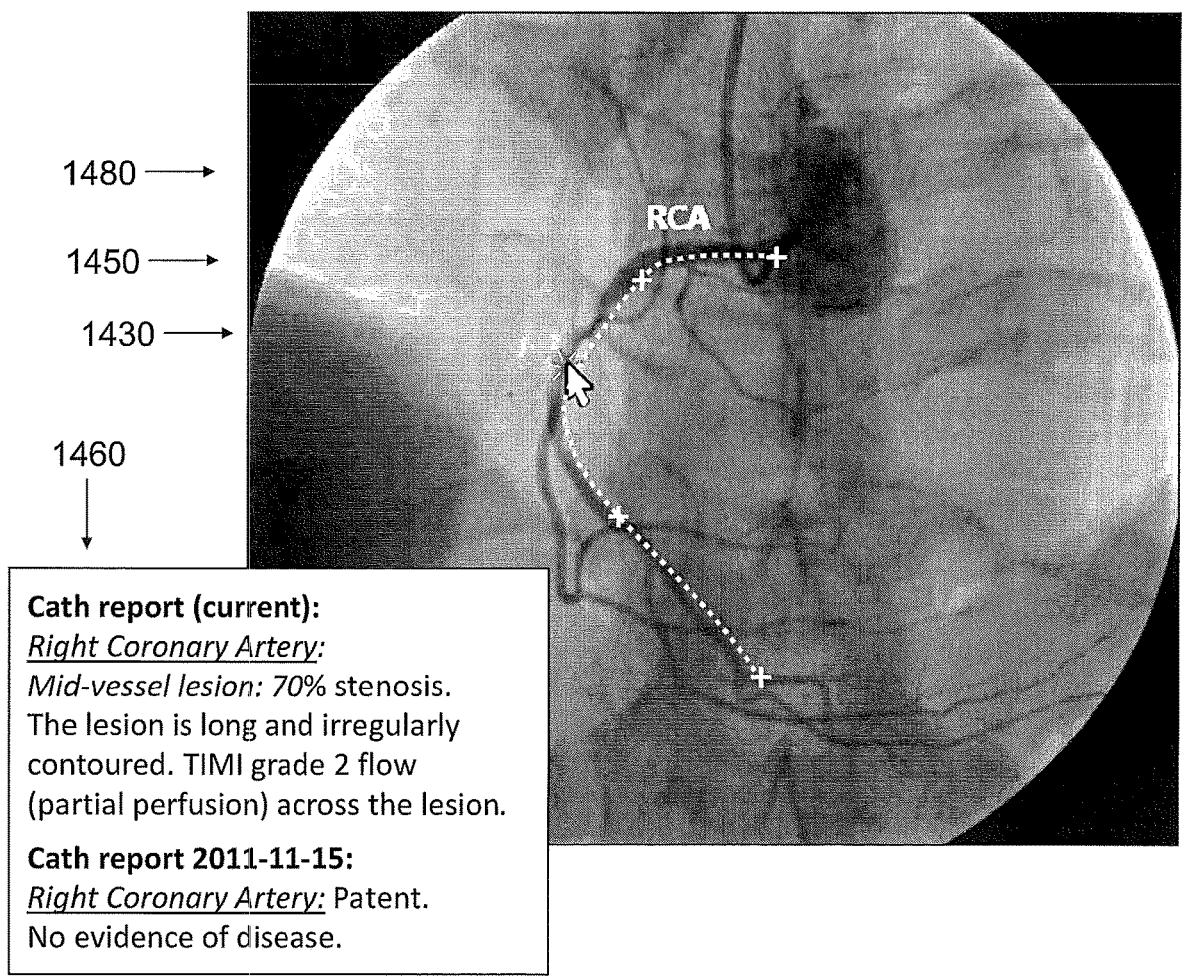
FIG. 14 illustrates an example of how a structured image prepared through the use of one embodiment of the present invention may be used in order to obtain additional information about an anatomical feature or pathology.

Certain embodiments of the present invention advantageously allow historical information and data for a patient to be associated and easily accessed with new information and data and one or more images of the patient. FIG. 14 illustrates a structured image 1480, the "asterisk" and arrow image on which are intended to show that, by selecting (e.g., "clicking" on, shown by an arrow and a partial asterisk) the image, a recorded structure data component 1460 can be seen. The data component 1460 illustrated in FIG. 14 includes a narrative, first describing the current condition of the anatomical feature and pathology in the area at which the selection occurred, then historical information describing the patient's past ("2011-11-15") condition.

Figure 15:
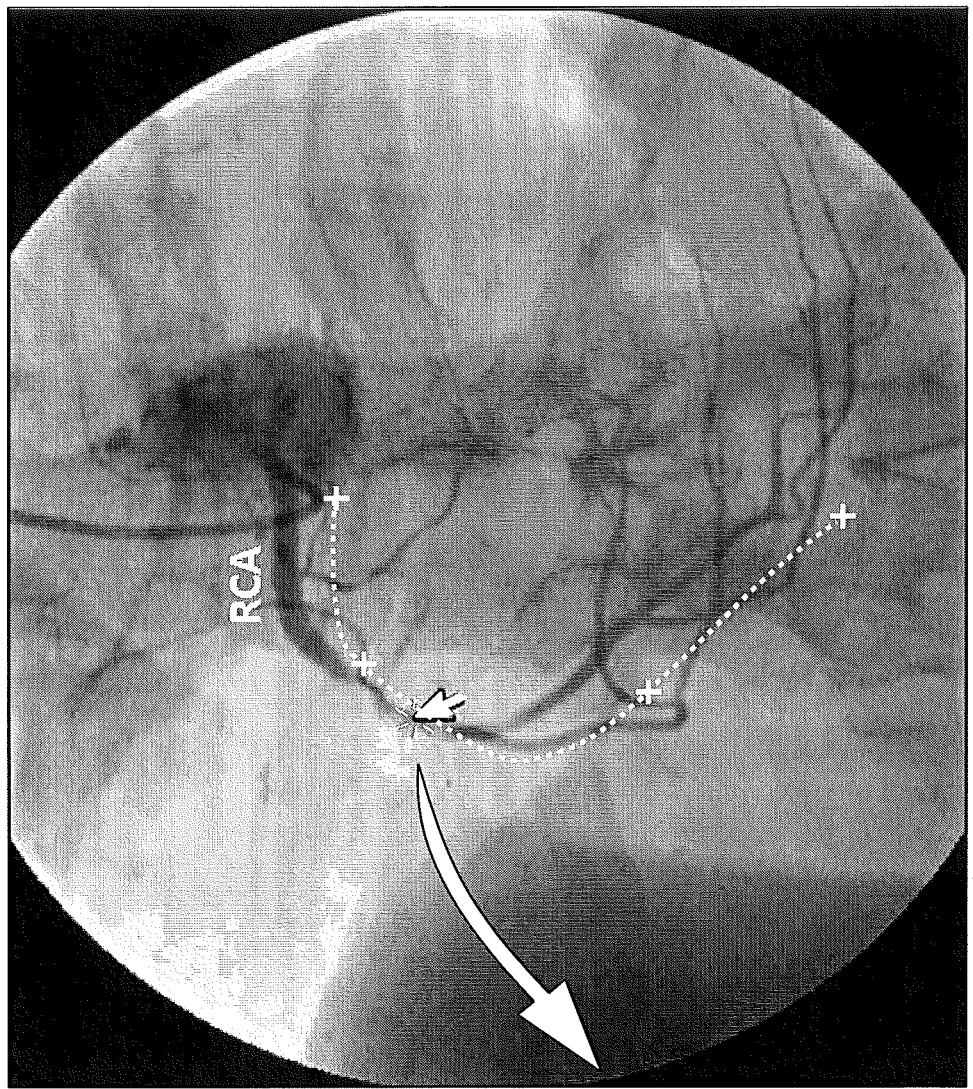
FIG. 15 illustrates an example of how a structured image prepared through the use of one embodiment of the present invention may be used in order to obtain one or more additional images related to an anatomical feature or pathology.
Figure 15:
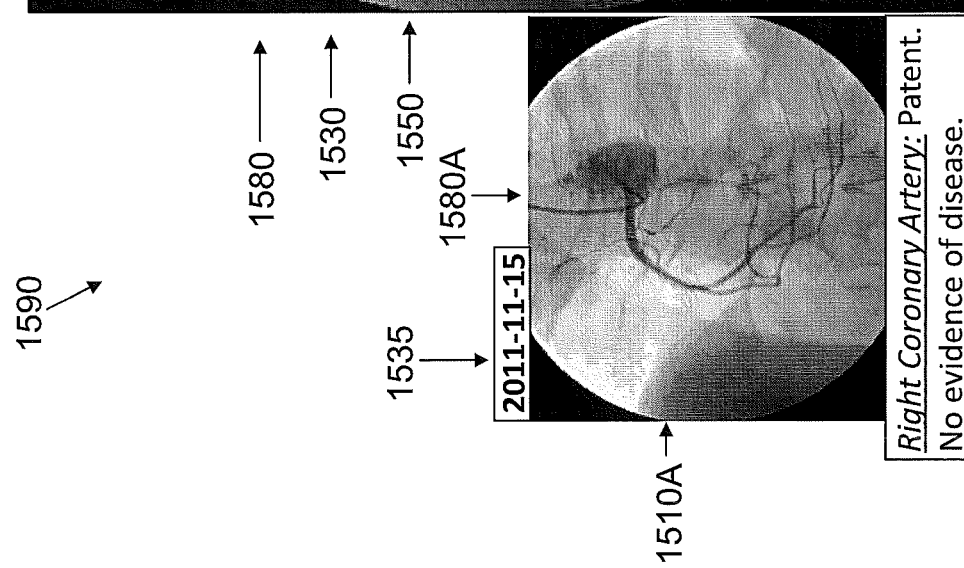

FIG. 15 illustrates an embodiment of the present invention that permits a user, by selecting (e.g., "clicking" on or near) a certain anatomical feature or pathology shown in the structured image 1580, to bring up and view another structured image 1580A providing additional information regarding the patient. Structured image 1580A in the illustrated embodiment is a historical image. Additional components of the present invention may provide additional information regarding the origins of the information, data, and images in the form of metadata or otherwise of that which is provided to a user. This information collectively identified in this application as "originating information". To illustrate, the structured image 1580A in the illustrated embodiment includes an originating information component 1535 in which the date on when the image was captured of the patient is shown. An additional information component—the caption 1570 in this example—provides information regarding the patient's condition at the time of the date provided in the originating information component 1535 in which the image 1510A was captured. The adjacent juxtaposition of the structured images 1580 and 1580A produces a structured image set 1590.

Figure 16:
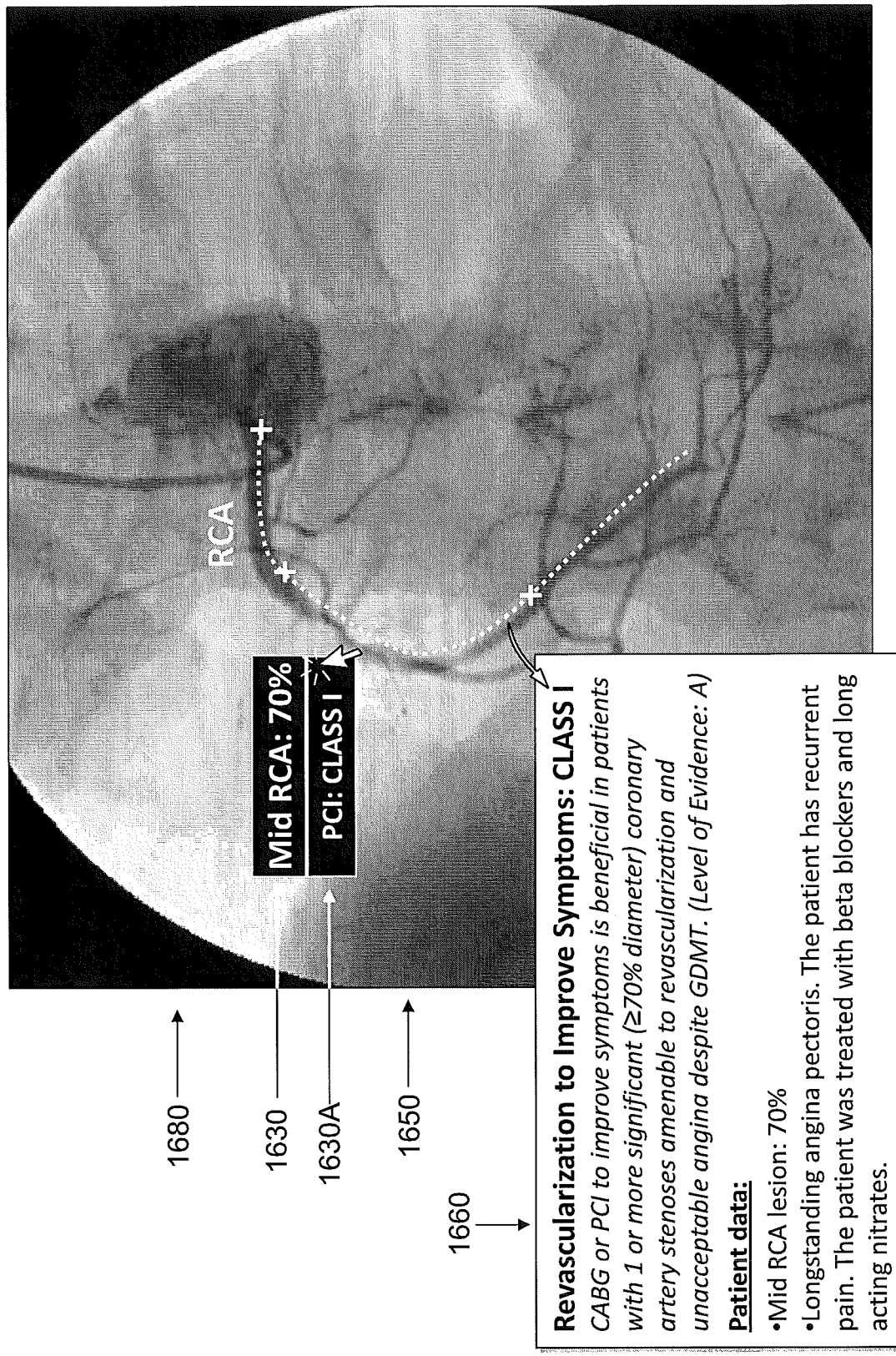
FIG. 16 illustrates an example of how a structured image prepared through the use of one embodiment of the present invention may be used in order to obtain additional information.

Certain embodiments of the present invention may facilitate the association of additional information that may be relevant to the possible diagnosis and treatment of an identified anatomical feature or pathology. FIG. 16 illustrates a structured image 1680 that includes a data information component 1630 that provides abbreviated data regarding the percentage of stenosis found in the patient's right artery and an assistance region 1630A informing the viewer that treatment information is available. In certain embodiments, the assistance region 1630A may be selected (e.g., by "clicking") so that additional information may be viewable by the user. In the embodiment illustrated in FIG. 16, the additional information is the relevant section of treatment guidelines that inform the user a recommended course of treatment given the data that was collected for the patient. The additional information may be presented in a variety of formats including the format of the narrative component 1660 shown in FIG. 16. Historical information regarding the patient may be presented to the user also by selecting the assistance region 1630A. In the FIG. 16 embodiment, the historical information—titled "Patient data"—is presented in the call out box 1660 with the treatment information.

Figure 17:
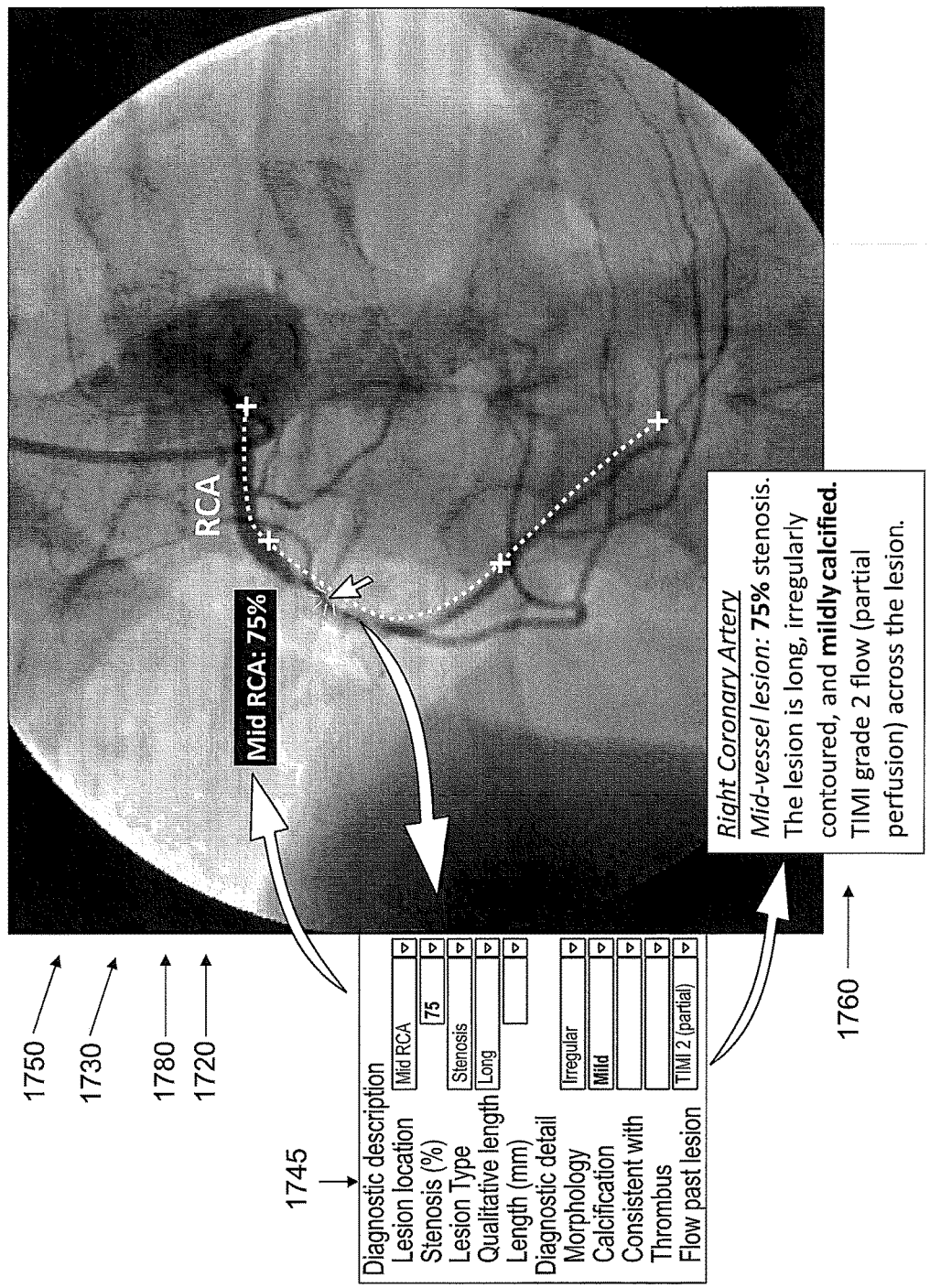
FIG. 17 illustrates an example of how a structured image prepared through the use of one embodiment of the present invention may be used in order to obtain a data entry form into which data may be recorded and from which a narrative may be produced.

Certain embodiments of the present invention may facilitate the efficient entry of data and the observations of a health care worker who is tasked with reading an image or images taken of a patient. Conventionally, to accomplish this task, a health care worker must work back and forth between the separate image or report form screens or documents. Certain embodiments of the present invention minimize the cognitive transitions and physical movements required of conventional methods of preparing an image report by permitting the appropriate reference frame 67 to be associated with a corresponding anatomical feature or pathology on a structured image such that a data entry form is presented to a user for recording structured data. FIG. 17 illustrates one embodiment of the invention in which the structured image 1780 is an angiographic image as the structured reference frame 1720 showing a right coronary artery. By selecting (e.g., "clicking on") the certain anatomical feature on structured image 1780 of right coronary artery, a data entry form 1745 is presented to the user. The data entry form 1745 may include may include data entry controls such as pick lists, checkboxes, numeric boxes, text boxes, and buttons, as well as mechanisms for displaying subordinate or sibling data entry forms such as pop-ups, pop-overs, split/merges, and dissolve/replaces. The tools may also include data from pre-existing statistical analysis of probabilities and reliabilities of a combination of similar case-studies to the associated medical procedure and data associated with the patient's current health and medical history. In certain embodiments of the present invention, a report narrative can be prepared from the structured data that is recorded through the use of the data entry form. Such preparation may be automatic upon entry of the data. Certain embodiments of the present invention automatically may update an earlier prepared report narrative and information that may be provided on the structured image's data presentation. In the FIG. 17 embodiment, the data entry form 1745 provides a narrative output 1760.

Certain embodiments of the present invention permit a user to select the portion of the image for which the user wishes to enter data not only by mouse, keyboard, or other devices but also by voice utterance. With respect to the embodiment shown in FIG. 17, the data entry form 1745 may be opened by the utterance of the phrase "Mid RCA". Once opened, the data entry form may be populated in part or whole by information delivered by voice. For a data entry form having picklist values, the voice utterances may simply be the selection of the appropriate value on the list.

Figure 18B:
FIG. 18B illustrates an example of the use of one embodiment of the present invention to distinguish a stenotic lesion pathology shown on a carotid ultrasound medical image.
Figure 18A:
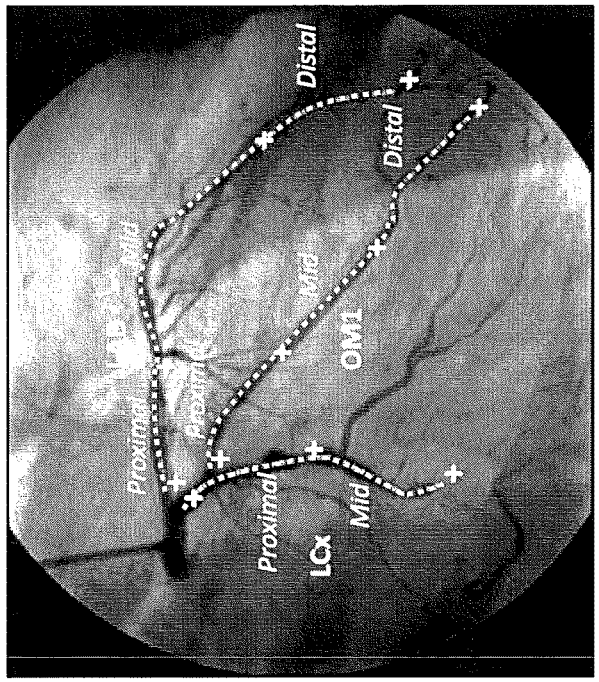
FIG. 18A illustrates an example of the use of one embodiment of the present invention to distinguish arteries on a coronary angiographic medical image.
Figure 18D:
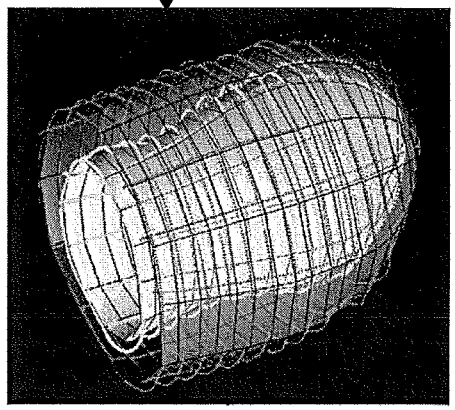
FIG. 18D illustrates a three-dimensional model of the left ventricle produced through the modeling of information obtained through the processing of cardiac MRI images of the left ventricle by one embodiment of the present invention.
Figure 18C:
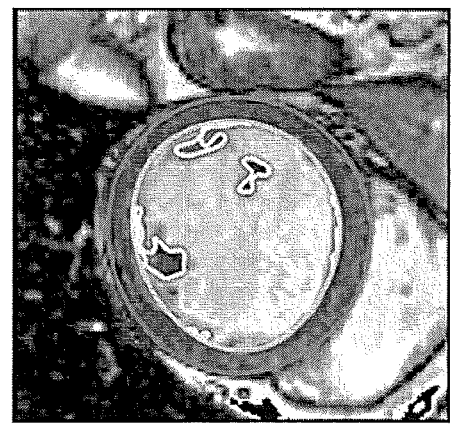
FIG. 18C illustrates an example of the use of one embodiment of the present invention to distinguish left ventricular features shown on a cardiac MRI medical image.

Certain embodiments of the present invention permit an anatomical feature or pathology to be selected and through the use of the appropriate reference frame, the position of the feature or pathology to be distinguished through the use of color, geometric shapes, geometric objects, or other graphical structure 1850 such as, but not limited to points, dots, lines, curves, regions, surfaces, and volumes. FIG. 18A illustrates a structured image 1880A in which a series of coronary arteries are distinguished as curving dashed lines. FIG. 18B illustrates a structured image 1880B in which a stenotic lesion in a carotid artery is distinguished by enclosing it in a boundary with a contrasting pattern. FIG. 18C illustrates a structured image 1880C in which the epicardial and endocardial surface boundaries of the left ventricle are distinguished as closed curves. Once distinguished, a user may interact with these graphical structures on-screen to retrieve, display, or record information about the features or pathologies that are associated with these graphical structures via the structured reference frame. Clicking on the geometric region in FIG. 18B, for instance, may display previously-recorded qualitative data about the associated stenotic lesion such as its morphology or calcification, including allowing for recording, editing, and storage of this information as structured data about the patient.

Certain embodiments of the present invention permit using the geometric properties of the graphical structure associated with a feature or pathology to manually or automatically compute quantitative properties of the feature or pathology. For example, the length of the major axis of the distinguished geometric region in FIG. 18B may be used to compute the length of the associated stenotic lesion. Similarly, the length of the region's minor axis (the dimension perpendicular to the region's major axis) may be used to compute the thickness of the lesion. The results of these computations using the structured image may then be stored as structured data about the patient.

Similarly, once the left ventricular epicardial (outer) and endocardial (inner) boundaries have been identified in FIG. 18C, the cross sectional area of the left ventricle (the area within the outer boundary), the left ventricular cavity (the area within the inner boundary), and the myocardium (the area between the boundaries) may be determined. The results of these computations using the structured image may then be stored as structured data about the patient.

Certain embodiments of the present invention permit a certain anatomical feature or pathology to be identified on a plurality of images and those images made available for efficient collective viewing at one time. The plurality of images may result from images captured of different views of a patient, or by different imaging or analytical systems, different imaging modalities, or at different times. This allows support for linking multiple views of a feature or pathology for subsequent retrieval or review. Embodiments of the present invention may permit all images of a selected anatomical feature or pathology to be viewable by a user on one screen automatically. The user may then compare views of a feature or pathology from different modalities or compare changes in a feature or pathology over time or in response to treatment, and/or combine images or reports to illustrate changes in a feature or pathology.

Figure 19:
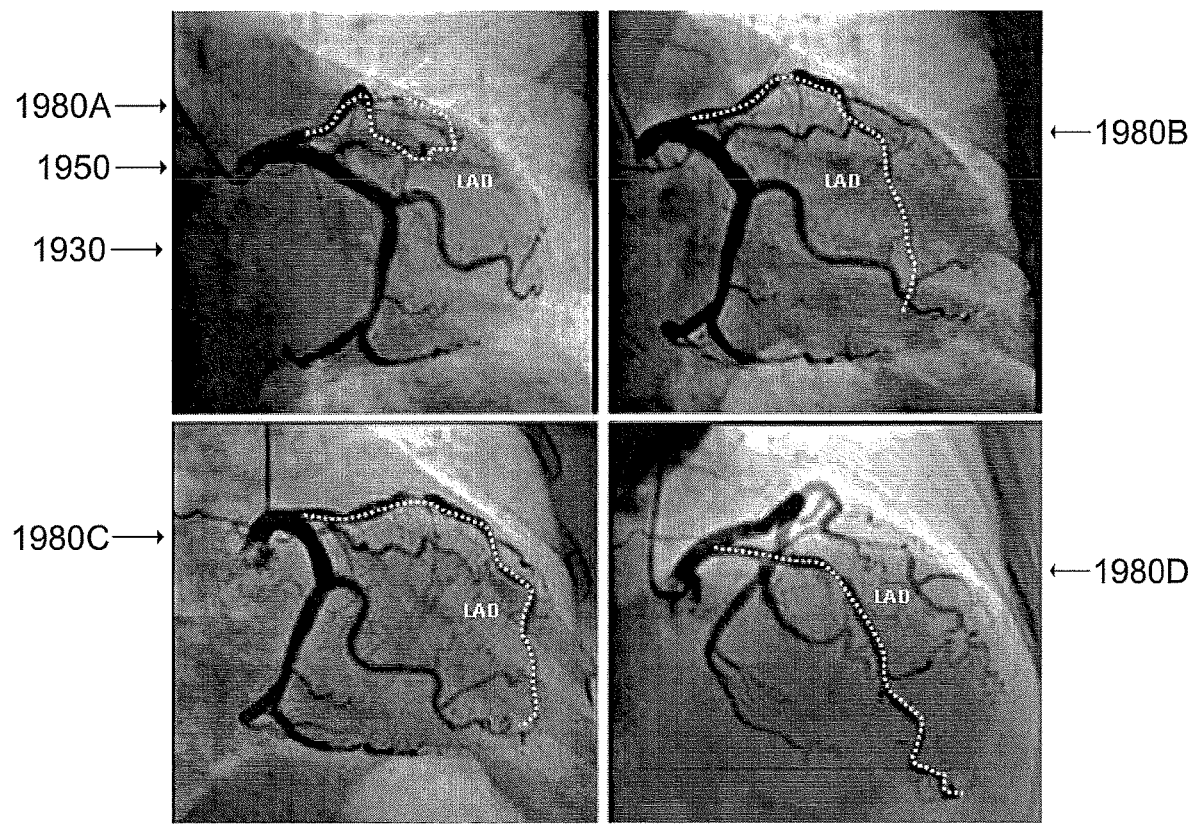
FIG. 19 illustrates an example of the use of one embodiment of the present invention to prepare a structured image set linking the position of the LAD in a set of coronary angiographic images showing different views of a patient's heart.

FIG. 19 illustrates an embodiment of the invention in which the structured reference frame is used to specify the position of the LAD in a series of coronary angiographic images 1980A, 19808, 1980C, and 1980D of a single patient taken from different perspectives. The position of the LAD in each image is distinguished by a graphical structure (dashed curve). The union of these graphical structures forms the basis of the structured reference frame that unifies these images into a structured image set 1930. Embodiments of the present invention permit a subsequent user interacting with image 1980A to click on the dashed curve corresponding to the LAD, whereupon the structured reference frame is used to identify the other images of the patient's LAD 1980B, 1980C, and 1980D, which are automatically retrieved and displayed on-screen, thereby yielding an efficient means of selecting and reviewing all of the imaging data in the current study related to the patient's LAD. In a clinical setting, the user specifying the location of the LAD (constructing the structured reference frame) may be a clinically-trained non-physician. The structured image sets resulting from their work thus improves the productivity of the highly-paid physicians who review the images during this and subsequent episodes of care.

Figure 20A:
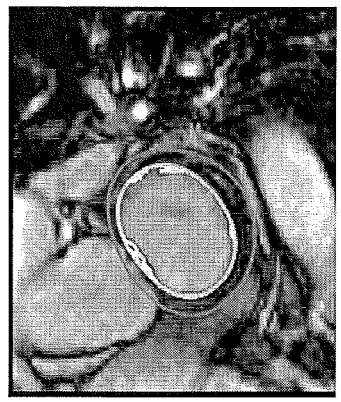
FIG. 20A illustrates an example of the use of one embodiment of the present invention to distinguish the left ventricular endocardial and epicardial borders shown on a slice of a cardiac MRI image.
Figure 20B:
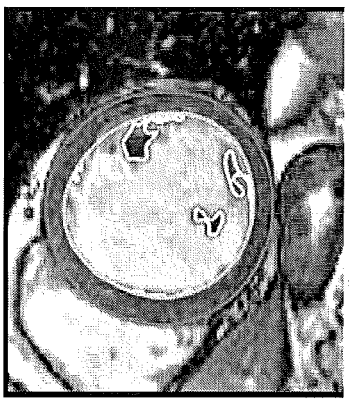
FIG. 20B illustrates an example of the use of one embodiment of the present invention to distinguish the left ventricular endocardial and epicardial borders shown on another slice of a cardiac MRI image.
Figure 20C:
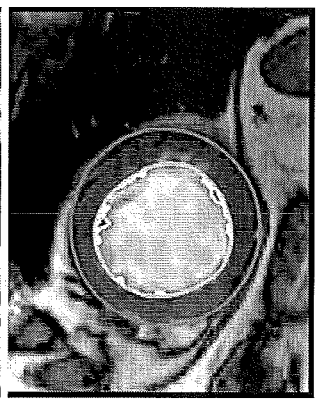
FIG. 20C illustrates an example of the use of one embodiment of the present invention to distinguish the left ventricular endocardial and epicardial borders shown on an additional slice of a cardiac MRI image.

Certain embodiments of the present invention may permit image processing such that boundaries, contours, shapes, or configurations of an anatomical feature or pathology are automatically detected and distinguished, and the structured reference frame automatically created for the user. FIG. 20A through FIG. 20C provide images processed through this component of certain embodiments of the invention. More specifically, FIG. 20A through FIG. 20C illustrate a cardiac MRI in which each image is a cross section ("slice") of the left ventricle. Intensity-based image segmentation techniques are applied to identify the region corresponding to the LV chamber (which contains blood) and the region corresponding to the LV mycocardium (which consists of muscle tissue). The outer boundary of the myocardial region is then used to define the contour of the LV epicardium, while the inner boundary of the myocardial region (or, equivalently, the outer boundary of the LV chamber) is used to define the contour of the LV endocardium. This process is repeated for each of the images ("slices") in FIG. 20A through FIG. 20C.

Figure 20D:
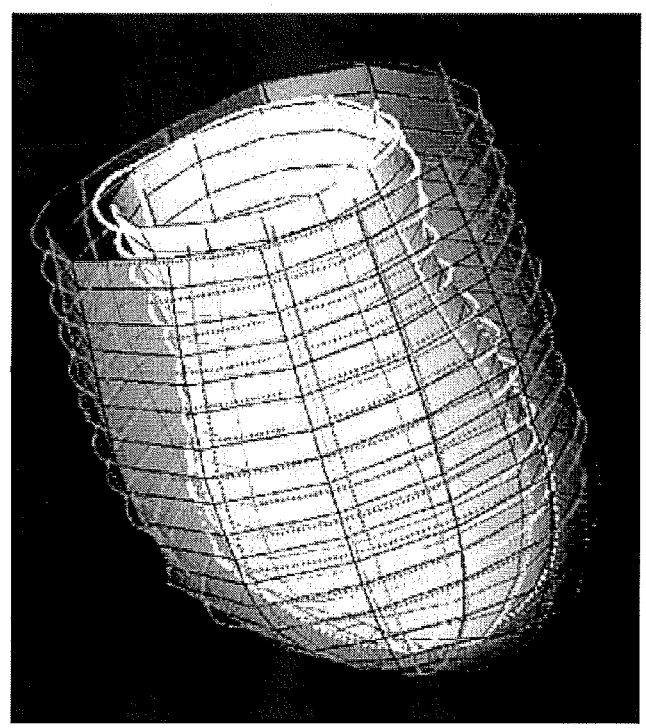
FIG. 20D illustrates a three-dimensional model of the left ventricular endocardial and epicardial borders produced through the modeling of information obtained through the processing of a set of slices from a cardiac MRI by one embodiment of the present invention.

In certain embodiments of the present invention, the information obtained through the processing of the one or more images may be combined to provide additional information. FIG. 20D illustrates the use of an embodiment of the invention by which the information from the processed images shown in FIG. 20A through FIG. 20C is combined to create a series of nested three-dimensional objects. Specifically, the LV epicardial (outer) contours are situated in three-dimensional space based on information in the structured reference frame, which describes the contours, and the MRI image set, which describes the position and orientation of the images (slices). These contours may then be connected to form a three-dimensional surface mesh modeling the LV epicardium. This procedure may then be repeated to form the surface mesh for the LV endocardium. The resulting three-dimensional cardiac model may be stored as part of the structured reference frame for later retrieval and review. In addition. the volumes enclosed by the LV epicardial and LV endocardial surfaces may be used to compute the LV myocardial volume and LV chamber volume, which may be stored as structured data about the patient.

Figure 21:
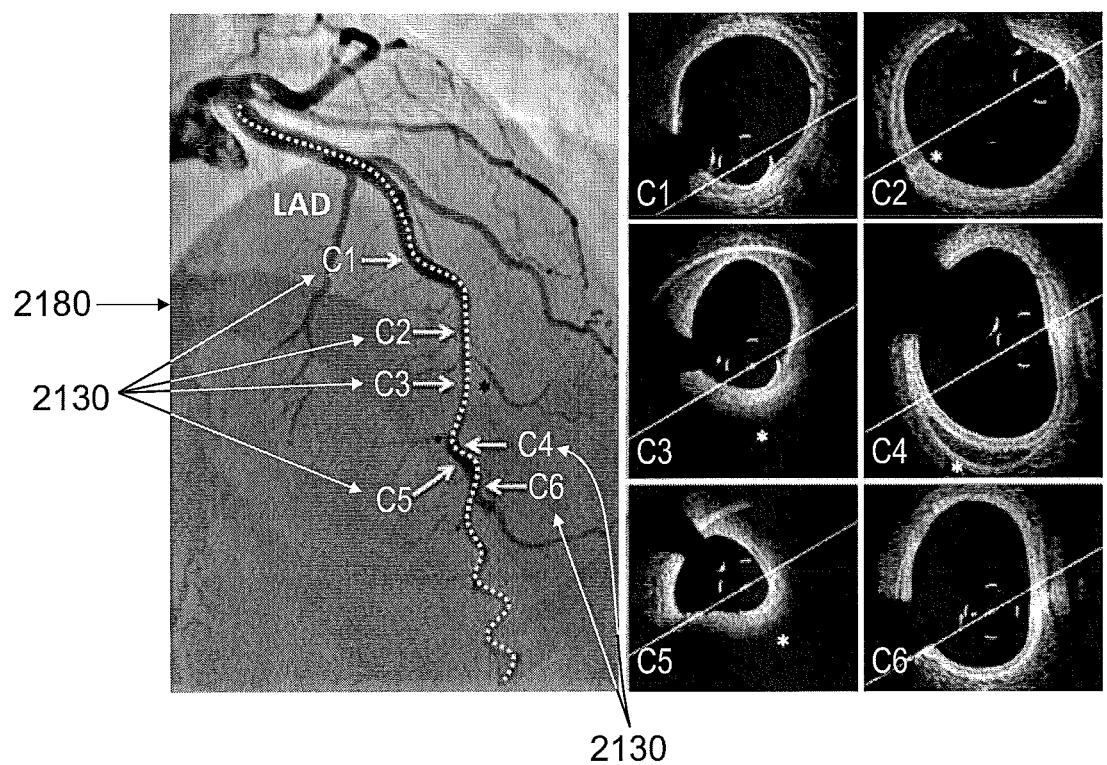
FIG. 21 illustrates an example of a coronary angiographic medical image of the LAD being associated with a set of optical coherence tomographic images taken at various points along the LAD through the use of a structured image set created by one embodiment of the present invention.

Certain embodiments of the present invention permit a structured reference frame to associate the position and geometric structure of an anatomical feature or pathology in images that were produced using different imaging modalities (e.g., x-ray, ultrasound, MRI). FIG. 21 illustrates a structured image 2180 consisting of coronary angiogram showing an x-ray view of the coronary arteries into which an x-ray contrast agent has been injected and a set of intracoronary Optical Coherence Tomography ("OCT") images showing ultrasonic views of the interior of the LAD taken at six points within the LAD.

In FIG. 21, a structured reference frame has been applied identifying the course of the LAD (denoted by the dashed curve) in the angiographic image and along which a set of landmarks (denoted by alphanumeric markers C1-C6) have been applied identifying points at which OCT images have been taken from within the LAD. A user reviewing the resulting structured image set may select one of these landmarks 2130 thereby triggering display of the associated OCT image for review. Alternatively, the physician performing the OCT procedure may reference the landmarks in the structured image set 2130 while recording the OCT images, thereby linking the OCT images or cineloops with the coronary angiogram. Prior to or during this review, measurements made on the OCT image (e.g., vessel diameter, stenosis thickness) can be automatically associated with the appropriate locations within the LAD via the mappings in the structured reference frame and the result saved as structured data associated with the patient. In a clinical setting, the technician participating in the image acquisition process could create the structured reference frame, thereby allowing the physicians who subsequently review the images to work with a single integrated structured image set and associated structured data set spanning multiple imaging modalities rather than with a set of disconnected images and cineloops.

Certain embodiments of the present invention extend the structured reference frame to include images of an anatomical feature or pathology taken at different moments in time, potentially include separate episodes of care spanning multiple years. The structured reference frame allows a user reviewing one image in the resulting structured image set to click on a distinguished geometric structure in one image so as to initiate the retrieval and display of the set of past and present images of the associated anatomical feature or pathology drawn from the structured image set, thereby providing a means of efficiently reviewing and evaluating changes in that feature or pathology over time. Measurements can be manually or automatically made on the images in the structured image set and the resulting data values related via the structured reference frame for storage as structured data about the patient and for use in assessing changes to the patient's health status over time.

Figure 22:
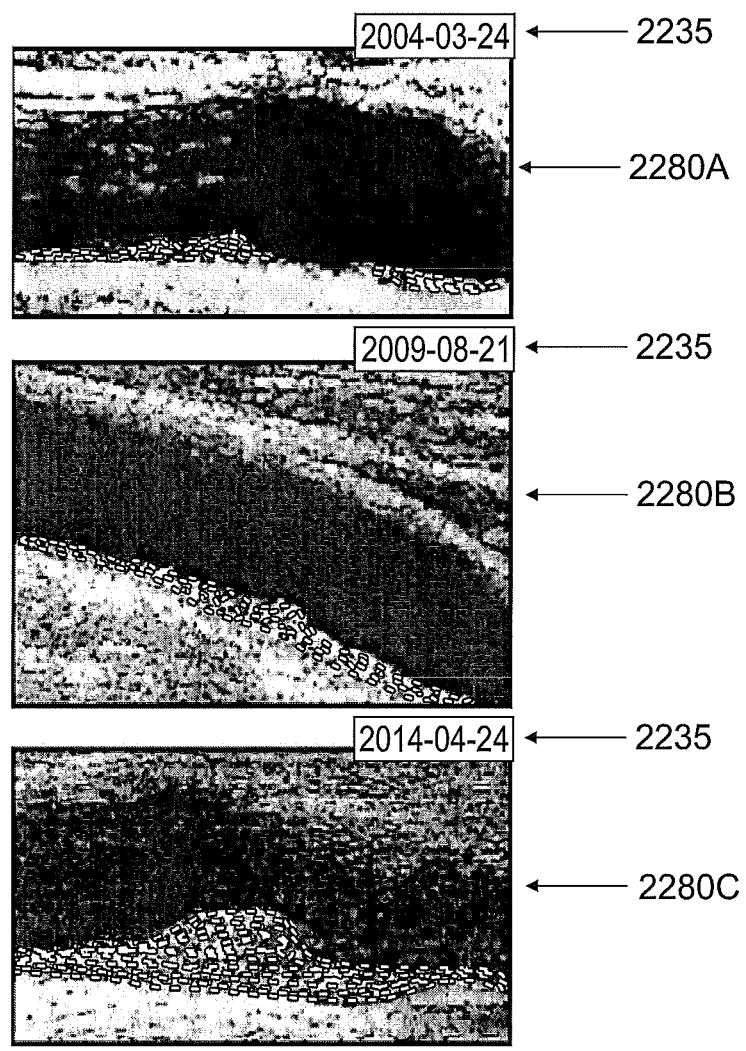
FIG. 22 illustrates a set of ultrasound images of a stenotic carotid lesion defined by a structured image set created by one embodiment of the present invention.

FIG. 22 shows a set of ultrasound cross-sectional images 2280A, 2280B, and 2280C of a carotid artery of a patient taken over a ten year period of time in which the position and extent of a stenotic lesion in each image has been identified by enclosing it within a region boundary with a contrasting pattern. Each of the images 2280A, 2280B, 2280C includes an originating information component 2235 showing the date of capture of each of the images. The length and thickness over the stenotic lesion may be manually or automatically computed based on the length of the major and minor axis respectively of the distinguished region and stored as structured data for the patient. A user reviewing one of these images may click the distinguished region to trigger display of the associated images, as well as display of a tabular or graphic presentation showing changes in the lesion length and thickness over time.

Figure 23:
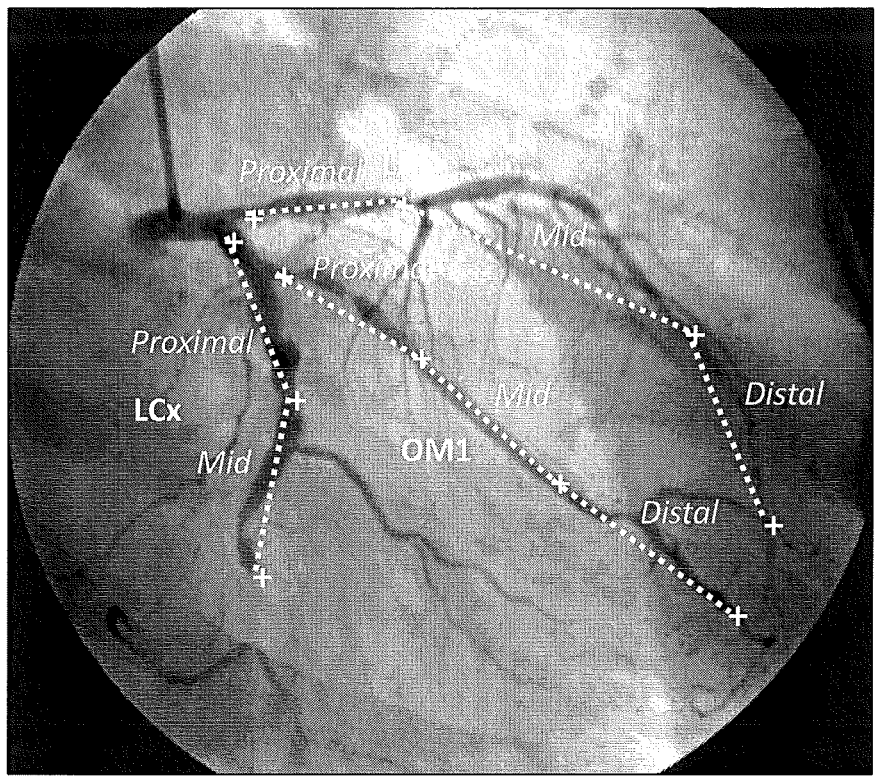
FIG. 23 illustrates the production of a structured reference frame for a coronary angiogram using a semi-automated method through the use of one embodiment of the present invention.
Figure 23:
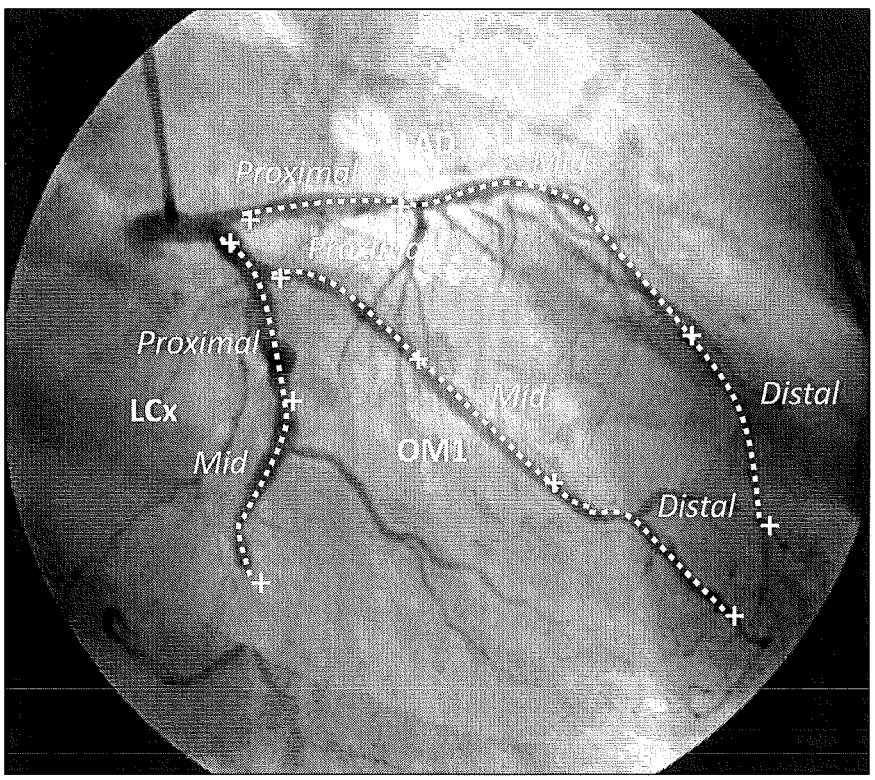

Certain embodiments of the present invention facilitate the review, analysis, preparation of reports regarding, and ultimately recommending treatment options to a patient by allowing a user to quickly create a structured reference frame on one or more images taken of a patient. FIG. 23 illustrates one embodiment of the present invention that shows the results of a semi-automatic process for creating a structured reference frame for the illustration of coronary angiogram images. A user of this embodiment begins with selection of the angiographic projection from information in the image's header (if available) or from the user (if not). The structured vessel reference standard for the identified angiographic projection specifies the vessels typically shown in the selected projection, along with their mapping to the structured knowledge base. In the projection shown in FIG. 2380A, the structured vessel reference standard would include the left main artery (LM), left anterior descending artery (LAD), left circumflex artery (LCx), and first obtuse marginal artery (OM1). The user is then prompted to identify each vessel segment in the selected projection based on their relative order in the coronary tree. In the example shown in FIG. 2380A, this progression would proceed as follows: proximal LM, mid LM, distal LM, proximal LAD, mid LAD, distal LAD, proximal LCx, mid LCx, distal LCx, proximal OM1, mid OM1, and distal OM1. After each prompt, the user may select (e.g., by "clicking" on) the location of the endpoint of the corresponding vessel segment (e.g., proximal LAD) on the angiographic image. The resulting "anchor" points are depicted as "+" signs in FIG. 2380A. These anchor points are then automatically connected by a series of line segments. The resulting piecewise linear approximations of the LM, LAD, LCx, and OM1 vessels define the initial structured reference frame for this image.

Certain embodiments of the present invention permit a process in which this initial structured reference frame is iteratively refined to better approximate the patient's anatomy. In the case of the image in FIG. 2380A, this refinement may consist of applying one of various non-linear interpolating curves (e.g., Bezier or B-spline curves) to more accurately trace the vessel paths. This refinement procedure is illustrated in FIG. 2380B, where the piecewise linear approximations of FIG. 2380B have been replaced with Bezier curves and these curves have been manually aligned with each vessel by adjusting the position of the "anchor" points that define the points of interpolation and by adding and positioning "control" points that specify the position and curvature of the Bezier curve. The interpolated curves and their associated vessel segments are mapped to the corresponding knowledge base descriptors and these mappings are incorporated into the structured reference frame. The resulting process yields a set of graphical structures (curves, in this case) that model the vessels in a coronary angiogram with the application of far less effort by the user than the manual tracing of vessel paths on the angiogram would require.

Certain embodiments of the present invention support the use of speech recognition to select the anatomical feature or pathology to be modeled by a graphical structure. A user presented with the coronary angiogram shown in FIG. 2380A begins by speaking aloud the name or abbreviation of a vessel (e.g., "Left Circumflex", "LAD"), whereupon the next four clicks on the image would automatically construct a graphical structure (curve) approximating the vessel as shown in the image and associate this graphical structure with the structured data and attributes of the vessel in the structured knowledge base. This procedure is repeated for each vessel shown in the image, optionally followed by—or interwoven with—refinement using non-linear curves (FIG. 2380B).

Certain embodiments of the present invention permit informative elements such as text descriptors, callout boxes, geometric shapes, icons, and/or additional data to be inserted to fully describe the structure and function of the designated anatomical feature. These informative elements may be added by selecting items from an on-screen menu, typing in text, or speaking text aloud to a speech recognition function, optionally followed by positioning of an element on-screen. The resulting informative elements are then automatically associated with the structured reference frame Creation of a structured reference frame can be made more efficient by using automated image segmentation techniques to extract objects of interest on an image. Embodiments of the present invention may use one of a variety of automated image segmentation techniques to identify objects of interest in an image depending on the imaging modality and the feature or pathology to be extracted.

Figure 24:
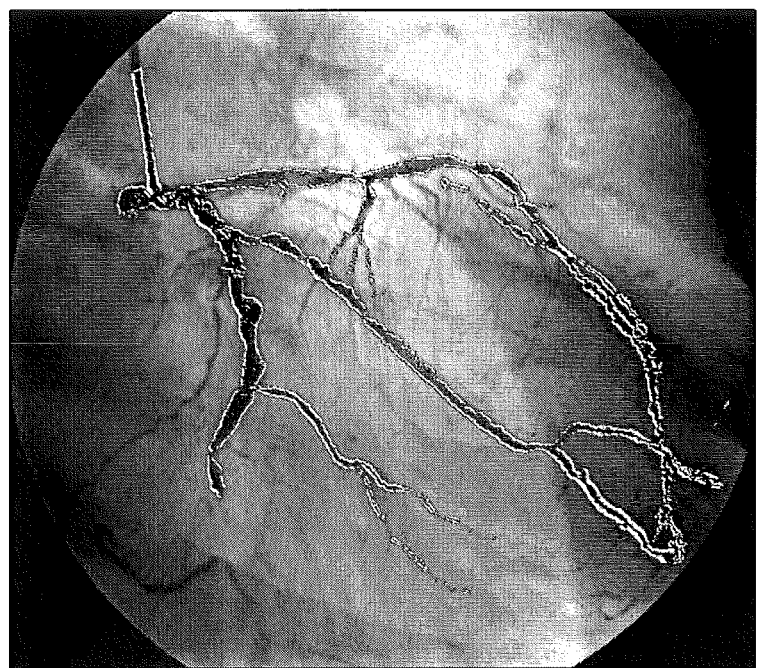
FIG. 24 illustrates the production of a structured reference frame for a coronary angiogram using automated image segmentation through the use of one embodiment of the present invention.
Figure 24:
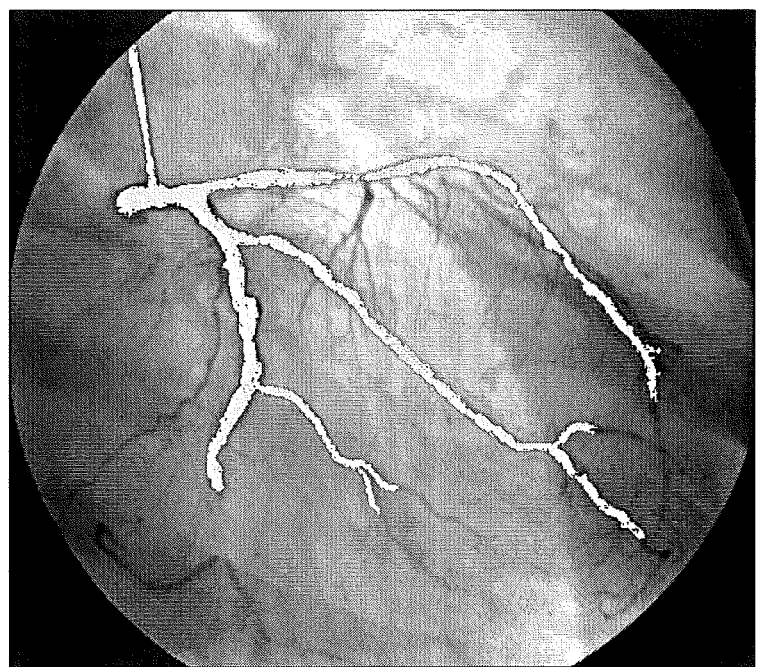

Certain embodiments of the present invention may include an image segmentation system by which the edges of an anatomical feature or pathology shown in an image may be automatically detected. Such systems use Canny, Laplace-Gaussian, or another edge detection method. FIG. 24 illustrates an image 2480A showing a coronary angiogram in which the borders of the arteries are identified through the use of an edge detection component and, after optional additional processing (e.g., edge optimization), continuous vessel borders are created.

Certain embodiments of the present invention may include an image segmentation system by which the vessels themselves are automatically detected. Such systems may use Hessian vesselness filtering, region growing, graph cutting, or another image segmentation method. Image 2480B illustrates the use of certain embodiments of the present invention to automatically detect (segment) the tubular vessels. followed by optional additional processing such as thinning or centerline creation.

Figure 25:
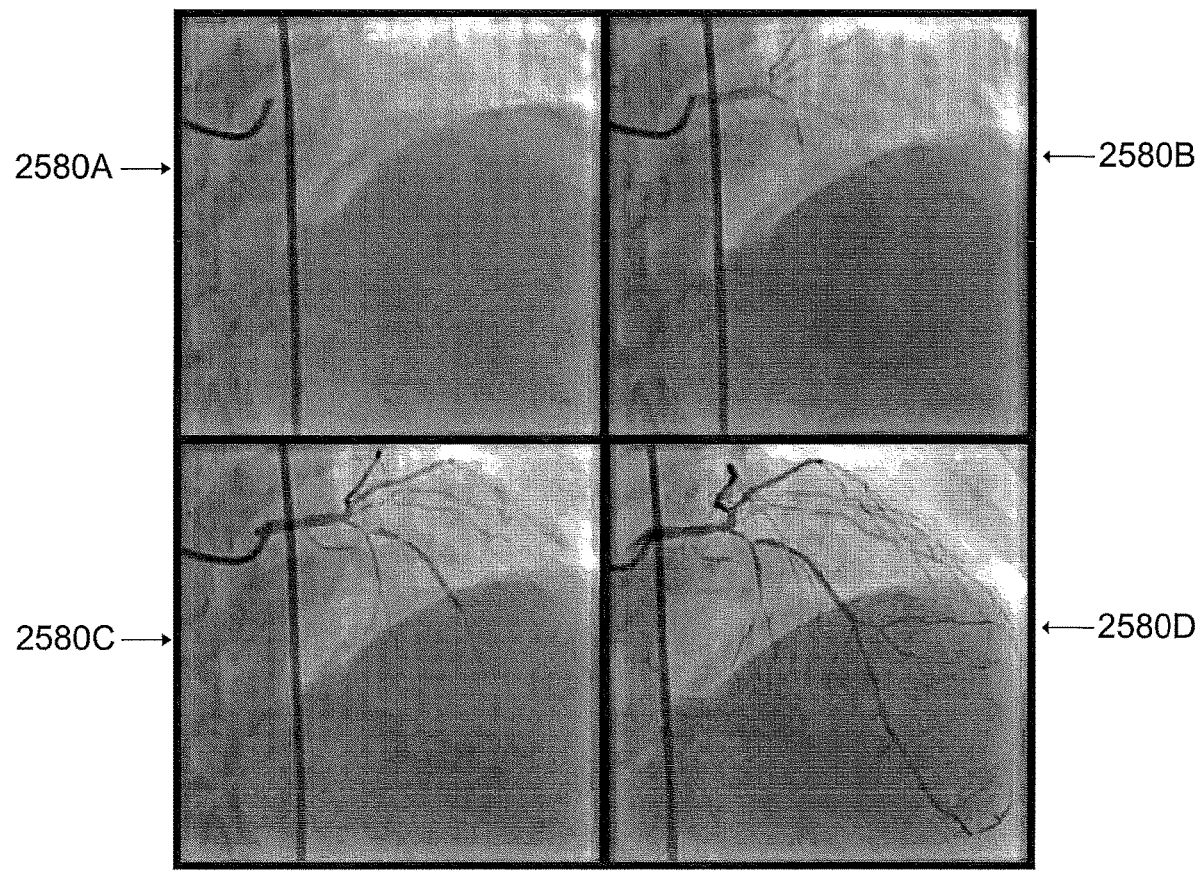
FIG. 25 illustrates the production of a structured reference frame for a sequence of coronary angiograms using automated image segmentation applied to track the flow of a contrast agent through the coronary arteries by one embodiment of the present invention.

Certain embodiments of the present invention may permit using the flow of contrast agent through the coronary vessels in a sequence of angiographic images to automatically determine the position of the vessels. FIG. 25 show a sequence of angiographic images 2580A, 2580B, 2580C, and 2580D taken while a contrast agent administered to a patient progresses through the coronary arteries of the patient. The difference between consecutive pairs of images highlights the path that the contrast agent has followed between pairs of images or, equivalently, the section of the coronary arteries made newly visible in the second image in each pair. Combining (overlaying) these differences reveals the path of coronary arteries in the angiogram. This procedure may be followed by optional additional processing such as thinning or centerline creation.

Figure 26:
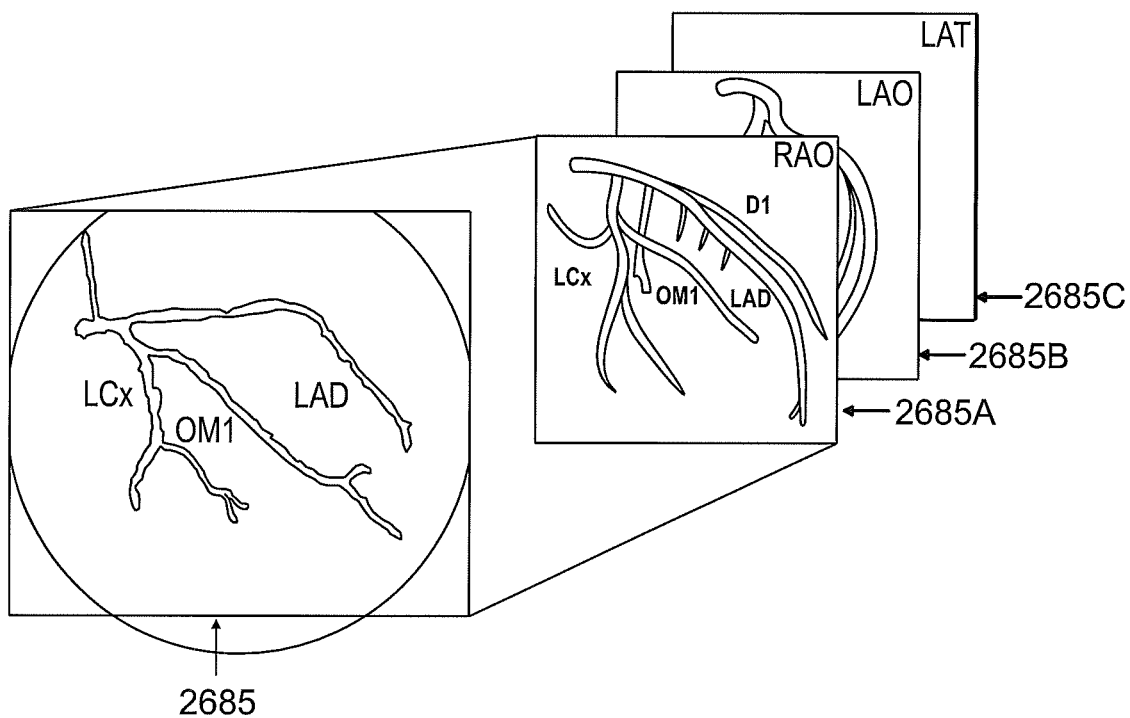
FIG. 26 illustrates the production of a structured reference frame for a coronary angiogram by image segmentation and template matching through the use of one embodiment of the present invention.

After particular anatomical features or pathologies have been detected by automated image segmentation techniques, certain embodiments of the present invention allow additional processing of the segmented images to be performed to identify the anatomical features or pathologies shown in the image. Embodiments of the present invention may allow such additional processing to be performed manually by a user selecting, recording, or speaking aloud the identifier or descriptors of the feature or pathology. Further embodiments of the present invention support automatic identification of the anatomical feature or pathology, including the application of relevant descriptors. FIG. 26 illustrates the use of an embodiment of the present invention that automatically identifies the vessels in a segmented coronary angiogram by comparing the segmented angiogram with a set of templates derived from a set of reference angiographic projections. The segmented angiogram 2685 is compared against templates 2685A, 2685B, and 2685C. The illustrated angiogram 2685 and the template 2685A are most similar (match) and therefore template 2685A is chosen as the reference template and, based on this reference template, the individual vessels shown in angiogram 2685 are identified. Certain embodiments of the present invention use a variation of this procedure in which a segmented image is compared against a database of previously-processed images and the closest matching image determined. The vessel identifications from the matching image are then applied to the new image. Once a user confirms these identifications, the new image is added to the database for use in future comparisons.

Certain embodiments of the present invention may be used for other imaging modalities and medical domains. Among such imaging systems for which the present invention may be used include echocardiography, transesophageal echocardiography, vascular ultrasound, coronary angiography, vascular angiography, nuclear cardiology imaging, coronary CT angiography, and cardiovascular MRI.

In addition to supporting reporting platforms combining structured reporting and image display/review in one system, embodiments of the proposed invention support reporting platforms in which the image acquisition, distribution, and review functions are handled by a dedicated imaging system that is separate from, but integrated with, the reporting system. This integration is accomplished by providing software packages based on structured image sets that the imaging system vendor uses to integrate their system with the reporting system.

One software package is based on a data schema that defines a set of structured imaging objects corresponding to anatomical features and pathologies. For each object, the schema specifies: display primitive identifiers, display labels, identifiers and a set of objects inclusive of smaller objects. The display primitive identifiers includes, for example, point, ROI, line, curve, region, shell, volume, etc. used to display the object. The display labels are user-readable labels for the objectives. The identifiers are machine-readable identifiers for an object. The set of objectives inclusive of smaller objects allows for hierarchical structure of multiple objects. The data schema defines a structured data set that must be displayed over each native structured reference frame that will serve to trigger system actions in response to user actions.

A second software package is based on an applications program interface that defines software interactions between the imaging system and the structured reporting application. This software package allows for: functions called by the structured reporting application to synchronize the imaging system, functions called by the imaging workstation to initialize the integration, functions called by the imaging workstation to display information, and functions called by the imaging workstation to record data. The functions called by the structured reporting application to synchronize the imaging system allow for opening and closing a designated study. The functions called by the imaging workstation to initialize the integration include: retrieval of data schema for an imaging modality, and retrieval of the set of structured imaging objects for a specified study. The functions called by the imaging workstation to display information include: retrieval of the set of imaging studies associated with a specified object; retrieval and/or display of the report data associated with a specified object; and retrieval and/or display of the notifications associated with a specified object. The functions called by the imaging workstation to record data include: displaying the data entry form for a specified object; retrieving the data entry form for a specified object; and submitting data for a specified object.

To prepare a structured image set for use in a clinical report, a physician will first select candidate images to use in a report. The selected images will serve as the structured reference frames. A technician will then create the structured reference set by identifying the anatomical regions of interest on the structured reference frames and incorporate structured reference data onto the structured reference frames as specified by the physician. The system imports data from a hemodynamics system and either manually or automatically additional data is populated, such as descriptive callout boxes, additional text descriptions and similar visual aids to describe processes, procedures or show changes over time or space. A user can additionally adjust any structured reference data upon the structured reference frame and can also adjust the visual appearance of the one or more structured reference frame contained within the structured reference set. The resulting structured reference set may then be logged as a clinical report and utilized in the normal course of business.

Figure 27:
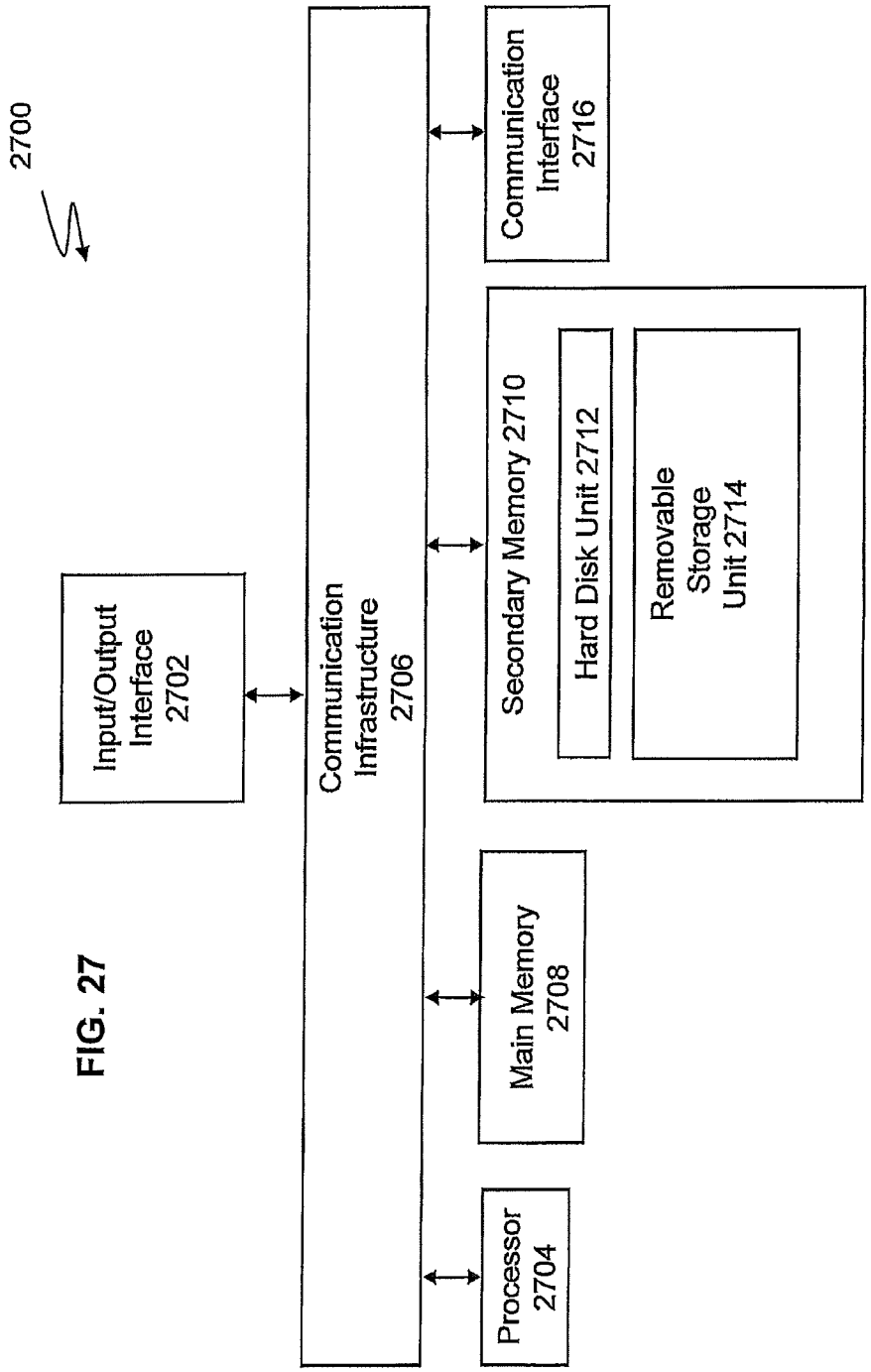
FIG. 27 illustrates a flow chart of a computing subsystem according to one embodiment of the present invention.

FIG. 27 illustrates an exemplary computer system 2700, or network architecture, that may be used to implement the system and methods according to the present invention. One or more computer systems 2700 may carry out the methods presented herein as computer code. One or more processors, such as processor 2707, which may be a special purpose or a general-purpose digital signal processor, is connected to a communications infrastructure 2706 such as a bus or network. Computer system 2700 may further include a display interface 2702, also connected to communications infrastructure 2706, which forwards information such as graphics, text, and data, from the communication infrastructure 2706 or from a frame buffer (not shown) to display unit. Computer system 2700 also includes a main memory 2708, for example random access memory (RAM), read-only memory (ROM), mass storage device, or any combination thereof. Computer system 2700 may also include a secondary memory 2710 such as a hard disk drive 2712, a removable storage drive, an interface, or any combination thereof. Computer system 2700 may also include a communications interface 2716, for example, a modem, a network interface (such as an Ethernet card), a communications port, a PCM-CIA slot and card, wired or wireless systems, etc.

It is contemplated that the main memory 2708, secondary memory 2710, communications interface 2716, or a combination thereof function as a computer usable storage medium, otherwise referred to as a computer readable storage medium, to store and/or access computer software and/or instructions.

Removable storage drive reads from and/or writes to a removable storage unit 2715. Removable storage drive and removable storage unit 2715 may indicate, respectively, a floppy disk drive, magnetic tape drive, optical disk drive, and a floppy disk, magnetic tape, optical disk, to name a few.

In alternative embodiments, secondary memory 2710 may include other similar means for allowing computer programs or other instructions to be loaded into the computer system 2700, for example, an interface 2716 and a removable storage unit 2714. Removable storage units 2714 and interfaces 2716 allow software and instructions to be transferred from the removable storage unit 2714 to the computer system 2700 such as a program cartridge and cartridge interface (such as that found in video game devices), a removable memory chip (such as an EPROM, or PROM) and associated socket, etc.

Communications interface 2702 allows software and instructions to be transferred between the computer system 2700 and external devices. Software and instructions transferred by the communications interface 2702 are typically in the form of signals which may be electronic, electromagnetic, optical or other signals capable of being received by the communications interface 2702. Signals are provided to communications interface 2702 via a communications path. Communications path carries signals and may be implemented using wire or cable, fiber optics, a phone line, a cellular phone link, a Radio Frequency ("RF") link or other communications channels.

Computer programs, also known as computer control logic, are stored in main memory 2708 and/or secondary memory 2710. Computer programs may also be received via communications interface 2716. Computer programs, when executed, enable the computer system 2700, particularly the processor 2704, to implement the methods according to the present invention. The methods according to the present invention may be implemented using software stored in a computer program product and loaded into the computer system 2700 using removable storage drive, hard drive or communications interface 2716. The software and/or computer system 2700 described herein may perform any one of, or any combination of, the steps of any of the methods presented herein. It is also contemplated that the methods according to the present invention may be performed automatically, or may be invoked by some form of manual intervention.

The invention is also directed to computer products, otherwise referred to as computer program products, to provide software to the computer system 2700. Computer products store software on any computer useable medium. Such software, when executed, implements the methods according to the present invention. Embodiments of the invention employ any computer useable medium, known now or in the future. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, optical storage devices, Micro-Electro-Mechanical Systems ("MEMS"), nanotechnological storage device, etc.), and communication mediums (e.g., wired and wireless communications networks, local area networks, wide area networks, intranets, etc.). It is to be appreciated that the embodiments described herein can be implemented using software, hardware, firmware, or combinations thereof.

The computer system 2700, or network architecture, of FIG. 27 is provided only for purposes of illustration, such that the present invention is not limited to this specific embodiment. It is appreciated that a person skilled in the relevant art knows how to program and implement the invention using any computer system or network architecture.

The invention is also directed to computer products (also called computer program products) comprising software stored on any computer useable medium. Such software, when executed, at least in part, in one or more data processing devices, causes the data processing device(s) to operate as described herein. Embodiments of the invention employ any computer useable or readable medium, known now or in the future. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, optical storage devices, MEMS, nanotechnological storage device, etc.), and communication mediums (e.g., wired and wireless communications networks, local area networks, wide area networks, intranets, etc.). It is to be appreciated that the embodiments described herein can be implemented using software, hardware, firmware, or combinations thereof.

Figure 28:
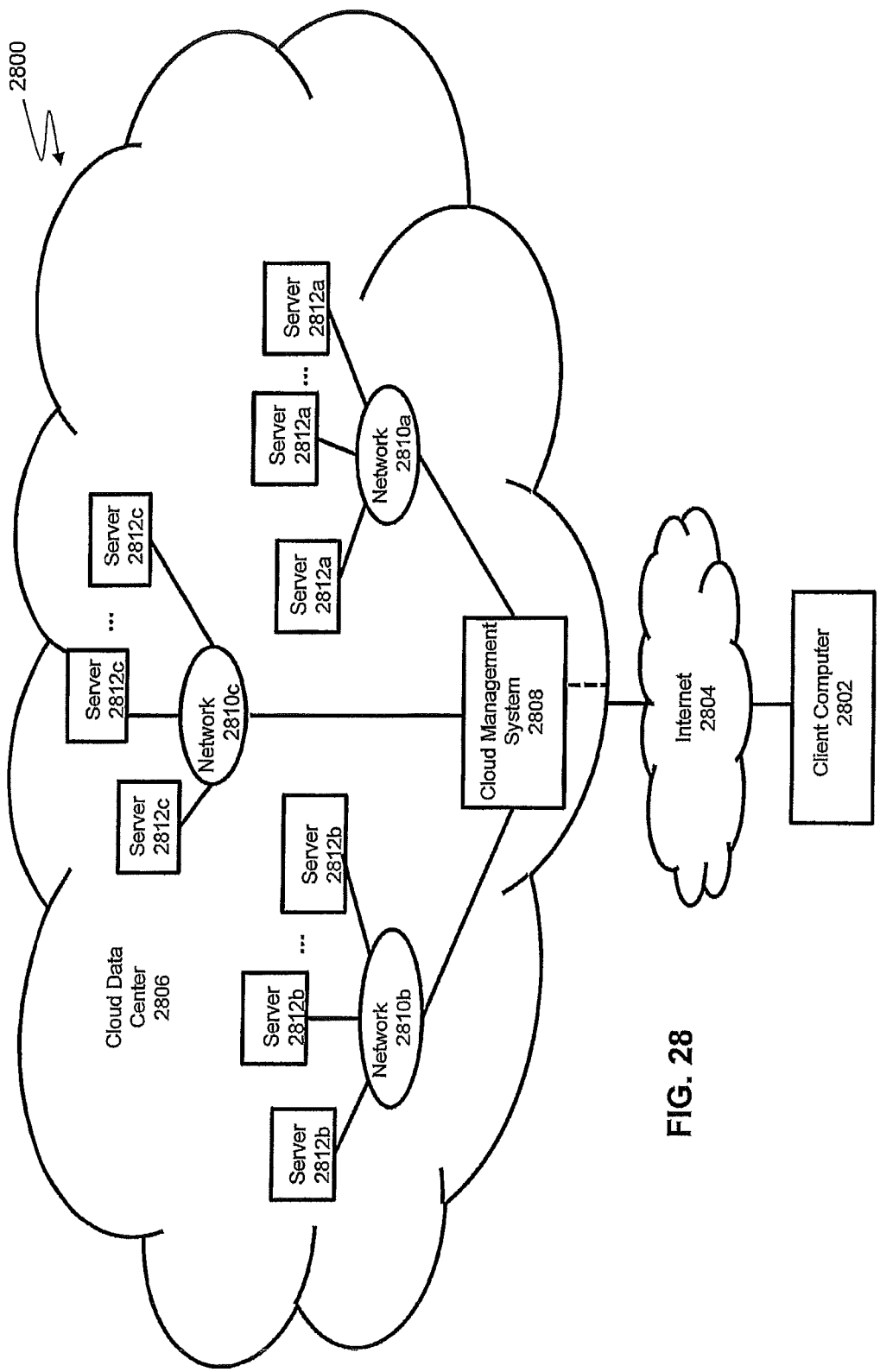
FIG. 28 illustrates a schematic diagram of a computing subsystem according to one embodiment of the present invention.

FIG. 28 illustrates an exemplary cloud computing system 2800 that may be used to implement the methods according to the present invention. The cloud computing system 2800 includes a plurality of interconnected computing environments. The cloud computing system 2800 utilizes the resources from various networks as a collective virtual computer, where the services and applications can run independently from a particular computer or server configuration making hardware less important.

Specifically, the cloud computing system 2800 includes at least one client computer 2802. The client computer 2802 may be any device through the use of which a distributed computing environment may be accessed to perform the methods disclosed herein, for example, a traditional computer, portable computer, mobile phone, personal digital assistant, tablet to name a few. The client computer 2802 includes memory such as random access memory ("RAM"), read-only memory ("ROM"), mass storage device, or any combination thereof. The memory functions as a computer usable storage medium, otherwise referred to as a computer readable storage medium, to store and/or access computer software and/or instructions.

The client computer 2802 also includes a communications interface, for example, a modem, a network interface (such as an Ethernet card), a communications port, a PCMCIA slot and card, wired or wireless systems, etc. The communications interface allows communication through transferred signals between the client computer 2802 and external devices including networks such as the Internet 2804 and cloud data center 2806. Communication may be implemented using wireless or wired capability such as cable, fiber optics, a phone line, a cellular phone link, radio waves or other communication channels.

The client computer 2802 establishes communication with the Internet 2804—specifically to one or more servers—to, in turn, establish communication with one or more cloud data centers 2806. A cloud data center 2806 includes one or more networks 2810*a*, 2810*b*, 2810*c* managed through a cloud management system 2808. Each network 2810*a*, 2810*b*, 2810*c* includes resource servers 2810*a*, 2810*b*, 2810*c*, respectively. Servers 2810*a*, 2810*b*, 2810*c* permit access to a collection of computing resources and components that can be invoked to instantiate a virtual machine, process, or other resource for a limited or defined duration. For example, one group of resource servers can host and serve an operating system or components thereof to deliver and instantiate a virtual machine. Another group of resource servers can accept requests to host computing cycles or processor time, to supply a defined level of processing power for a virtual machine. A further group of resource servers can host and serve applications to load on an instantiation of a virtual machine, such as an email client, a browser application, a messaging application, or other applications or software.

The cloud management system 2808 can comprise a dedicated or centralized server and/or other software, hardware, and network tools to communicate with one or more networks 2810*a*, 2810*b*, 2810*c*, such as the Internet or other public or private network, with all sets of resource servers 2812*a*, 2812*b*, 2812*c*. The cloud management system 1808 may be configured to query and identify the computing resources and components managed by the set of resource servers 2812*a*, 2812*b*, 2812*c* needed and available for use in the cloud data center 2806. Specifically, the cloud management system 2808 may be configured to identify the hardware resources and components such as type and amount of processing power, type and amount of memory, type and amount of storage, type and amount of network bandwidth and the like, of the set of resource servers 2812*a*, 2812*b*, 2812*c* needed and available for use in the cloud data center 1806. Likewise, the cloud management system 2808 can be configured to identify the software resources and components, such as type of Operating System ("OS"), application programs, and the like, of the set of resource servers 2812*a*, 2812*b*, 2812*c* needed and available for use in the cloud data center 2806.

The present invention is also directed to computer products, otherwise referred to as computer program products, to provide software to the cloud computing system 2800. Computer products store software on any computer useable medium, known now or in the future. Such software, when executed, may implement the methods according to certain embodiments of the invention. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, optical storage devices, Micro-Electro-Mechanical Systems ("MEMS"), nanotechnological storage device, etc.), and communication mediums (e.g., wired and wireless communications networks, local area networks, wide area networks, intranets, etc.). It is to be appreciated that the embodiments described herein may be implemented using software, hardware, firmware, or combinations thereof.

The cloud computing system 2800 of FIG. 28 is provided only for purposes of illustration and does not limit the invention to this specific embodiment. It is appreciated that a person skilled in the relevant art knows how to program and implement the invention using any computer system or network architecture.

While the disclosure is susceptible to various modifications and alternative forms, specific exemplary embodiments thereof have been shown by way of example in the drawings and have herein been described in detail. It should be understood, however, that there is no intent to limit the disclosure to the particular embodiments disclosed, but on the contrary, the intention is to cover all modifications, equivalents, and alternatives falling within the scope of the disclosure as defined by the appended claims.

Ideally, interpretation of a patient's medical images is done in conjunction with related data from the patient's medical record. For this to occur, retrieval and review of the related data must be an intuitive and efficient process.

A structured image set's reference frame can be used to map a selected location on a structured image to an anatomical feature or pathology and to the data elements (descriptors) associated with that feature or pathology. Recorded instances of these data elements can then be automatically retrieved and the report narrative for each recorded instance displayed on-screen for review by the user. Similarly, recorded instances of these data elements can be used to create information and graphical data components that are displayed on-screen so as to appear integrated with the associated images. Note that these structured data elements can originate from various sources (e.g., imaging studies for various modalities, clinical notes) and from various points in time. Taken together, the retrieved structured data provides the reporting physician with an integrated longitudinal view of the selected anatomical feature or pathology.

Similarly, given a selected anatomical feature or pathology, a structured image set's reference frame can be used retrieve the set of images that are related to the selected feature or pathology for efficient review, including images from the current study, from prior studies, and from other imaging modalities.

The structured data set may be based on a combination of analytical tools to further describe the structured reference frame. The analytical tools may include data entry controls such as pick lists, checkboxes, numeric boxes, text boxes, and buttons, as well as mechanisms for displaying subordinate or sibling data entry forms such as pop-ups, pop-overs, split/merges, and dissolve/replaces. The tools may also include data from pre-existing statistical analysis of probabilities and reliabilities of a combination of similar case-studies to the associated medical procedure and data associated with the individual's current health and medical history. The structured data recorded with the data entry form is then used to update the report narrative and the structured image's data presentation.

What is claimed is:

1. A computer system for creating a structured image set derived from a plurality of actual patient medical images, comprising:
   a processor;
   a screen display;
   a main memory in communication with the processor via a communication infrastructure, said memory including stored instructions that, when executed by said processor, cause said processor to:
   receive one or more of the plurality of actual patient medical images that display anatomical features or pathologies and create one or more structured reference frames;
   retrieve a program code that allows for command code to generate one or more structured data sets from a knowledge base, wherein the structured data set comprises information directed to the anatomical features or the pathologies;
   analyze the one or more structured reference frames using the one or more structured data sets by mapping the anatomical features or the pathologies of the actual patient medical images to the information of the structured data set;
   generate the structured image set comprising both the one or more structured reference frames and the one or more structured data sets, the structured image set including a structured image object displayed on the actual patient medical images, the structure image object comprising a data information component or graphical data components associated with the anatomical features or pathologies, the data information component or the graphical data components positioned on the one or more structured reference frames; and
   display on the screen display the structured image set such that one or more health care worker may view and modify and add to information shown on the structured image set.

2. The system according to claim 1, wherein the communication infrastructure is configured to facilitate collaboration of a plurality of health care workers via the internet.

3. The system according to claim 1, wherein the system is configurable to permit integration of one or more historical actual patient medical images and contemporary actual patient medical images with a temporal structured image set to create for display the temporal structured image set.

4. The system according to claim 3, wherein the system is configurable to permit integration of the one or more historical actual patient medical images and the one or more contemporary actual patient medical images with one or more different views of the actual patient medical images to provide for display a spatiotemporal structured image set.

5. The system according to claim 1, further including a voice control component configurable to receive a user's voice instructions for control of the processor.

6. The system according to claim 1, wherein the one or more structured data sets are based on pre-existing statistical analysis of probabilities and reliabilities of similar case-studies to associated medical procedure.

7. The system according to claim 1, wherein the one or more structured data sets are based on pre-existing statistical analysis of probabilities and reliabilities of a patient's health and medical history.

8. The system according to claim 1, wherein the one or more structured data sets are based on pre-existing statistical analysis of probabilities and reliabilities of a combination of similar case-studies to the associated medical procedure and a patient's health and medical history.

9. The system of claim 1, further including a remote memory in which certain or all the one or more structured data sets are stored for access.

10. The system of claim 1, further including a component for the receipt and the distribution of certain or all the structured data sets.

11. The system of claim 1, further including an image processing component usable to facilitate the creation of the structured reference frame.

12. The system of claim 1, wherein the one or more structured data sets and the one or more structured reference frames are configurable to create the data information component or the graphical data components that are included in the one or more structured image sets.

13. The system of claim 1, wherein the one or more structured data sets and the one or more structured reference frames are configurable to create information data components that identify possible pathologies or treatments shown are in the one or more structured image sets.

14. The system of claim 1, wherein said processor is configurable to permit selection of an anatomical feature or pathology in the one or more structured image sets such that information about the selected anatomical feature or pathology from a structured data set, clinical reports, or other information sources is accessed and displayed to a user.

15. The system of claim 14, wherein the selection of the anatomical feature or pathology in the one or more structured image sets displays related images of the selected feature or pathology from historic or other actual patient medical images.

16. The system of claim 14, wherein the selection of the anatomical feature or pathology in the one or more structured image sets displays a data entry tool for recording or modifying data items related to the selected feature or pathology.

17. The system of claim 14, wherein the selection or recording of data describing the anatomical feature or pathology triggers retrieval of one or more actual patient medical images that include the selected feature or pathology.

18. The system of claim 17, wherein the selection or recording of data describing the anatomical feature or pathology triggers the creation of the data information component or the graphical data components that are displayed on the retrieved images.

19. The system of claim 1, wherein one or more structured image objects are positioned on the structured image set to track or circumscribe the anatomical features or the pathologies of the actual patient medical images.

20. The system of claim 19, wherein the one or more structured image objects is selected from the group comprising: points, lines, curves, regions, surfaces, volumes.

\* \* \* \* \*